United States Patent
Uchikawa et al.

(10) Patent No.: US 9,470,700 B2
(45) Date of Patent: Oct. 18, 2016

(54) AUTOMATIC ANALYZER

(71) Applicant: Toshiba Medical Systems Corporation, Otawara-shi (JP)

(72) Inventors: Asuka Uchikawa, Nasushiobara (JP); Shoichi Kanayama, Otawara (JP); Naru Ikeda, Tokyo (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 51 days.

(21) Appl. No.: 14/461,510

(22) Filed: Aug. 18, 2014

(65) Prior Publication Data

US 2014/0356235 A1 Dec. 4, 2014

Related U.S. Application Data

(63) Continuation of application No. PCT/JP2013/073448, filed on Aug. 30, 2013.

(30) Foreign Application Priority Data

Aug. 31, 2012 (JP) ................................. 2012-192587

(51) Int. Cl.
*G01N 35/02* (2006.01)
*G01N 35/00* (2006.01)
*G01N 21/51* (2006.01)
(Continued)

(52) U.S. Cl.
CPC .......... *G01N 35/0098* (2013.01); *G01N 21/51* (2013.01); *G01N 21/82* (2013.01); *G01N 2035/0439* (2013.01); *G01N 2035/0453* (2013.01); *G01N 2035/0455* (2013.01)

(58) Field of Classification Search
None
See application file for complete search history.

(56) References Cited

U.S. PATENT DOCUMENTS

| 4,725,140 A | * | 2/1988 | Musha | ............... G01N 21/21 356/336 |
| 5,186,827 A | * | 2/1993 | Liberti | .................. A23L 3/32 210/222 |
| 5,200,084 A | | 4/1993 | Liberti et al. | |

(Continued)

FOREIGN PATENT DOCUMENTS

| CN | 101319976 A | 12/2008 |
| CN | 101977692 A | 2/2011 |

(Continued)

OTHER PUBLICATIONS

Combined Office Action and Search Report issued Dec. 3, 2014 in Chinese Patent Application No. 201380001543.9 (with English language translation).

(Continued)

*Primary Examiner* — P. Kathryn Wright
(74) *Attorney, Agent, or Firm* — Oblon, McClelland, Maier & Neustadt, L.L.P.

(57) ABSTRACT

According to one embodiment, an automatic analyzer includes a magnet and a photometric mechanism. The magnet generates a magnetic field applied to a test solution containing a sample and magnetic particles accommodated in a cuvette. The photometric mechanism includes a light source and a detector. The light source irradiates light toward the test solution. The detector is provided in a position opposed to the light source across the cuvette to detect the light from the test solution. The magnet has a geometrical arrangement such that a magnetic flux density of the magnetic field in the test solution inside the cuvette becomes substantially uniform.

10 Claims, 21 Drawing Sheets

(51) Int. Cl.
 *G01N 21/82* (2006.01)
 *G01N 35/04* (2006.01)

(56) References Cited

U.S. PATENT DOCUMENTS

| | | |
|---|---|---|
| 5,705,062 A | 1/1998 | Knobel |
| 2010/0062433 A1 | 3/2010 | Nagaoka et al. |
| 2010/0273230 A1 | 10/2010 | Bhakdi et al. |

FOREIGN PATENT DOCUMENTS

| | | |
|---|---|---|
| EP | 2 177 271 A1 | 4/2010 |
| JP | 63-187157 A | 8/1988 |
| JP | 1-193647 A | 8/1989 |
| JP | 6-160401 A | 6/1994 |
| JP | 6-213900 A | 8/1994 |
| JP | 6-63150 U | 9/1994 |
| JP | 7-181188 A | 7/1995 |
| JP | 7-121330 B2 | 12/1995 |
| JP | 7-318559 A * | 12/1995 |
| JP | 7-318559 A | 12/1995 |
| JP | 08-178931 A | 7/1996 |
| JP | 09-325148 A | 12/1997 |
| JP | 11-326334 A | 11/1999 |
| JP | 2000-346843 A | 12/2000 |
| JP | 2009-168636 A | 7/2009 |
| WO | 2008-001868 A1 | 1/2008 |

OTHER PUBLICATIONS

International Search Report mailed Nov. 19, 2013 in PCT/JP2013/073448 filed Nov. 11, 2013 with English Translation.
International Preliminary Report of Patentability and Written Opinion issued Mar. 12, 2015 in PCT/JP2013/073448 (English translation only).

* cited by examiner

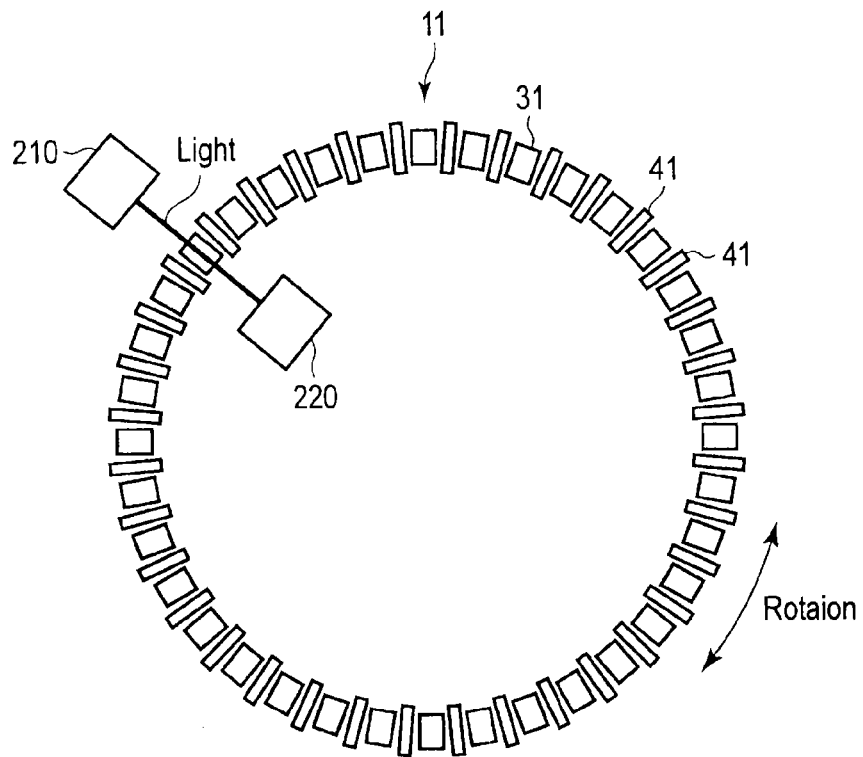
F I G. 2
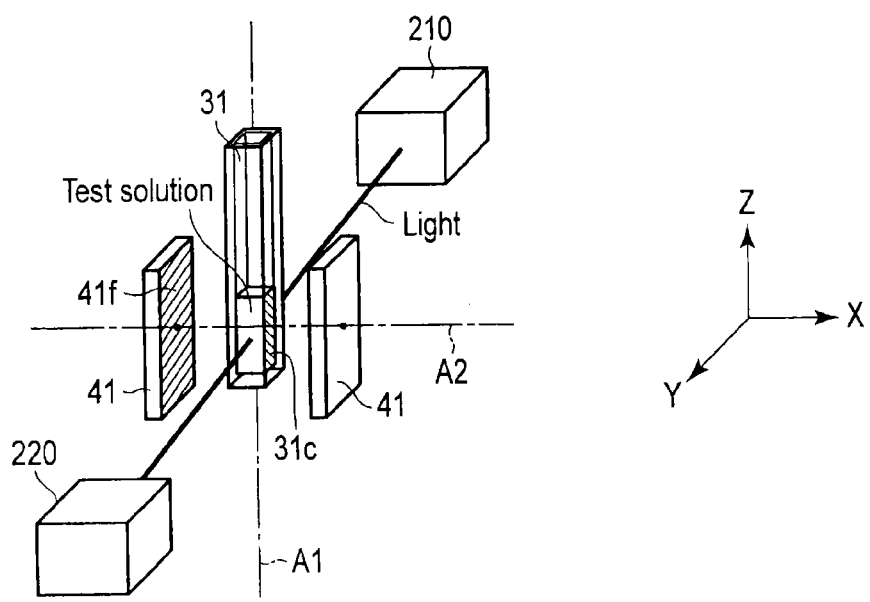
F I G. 3

The embodiment

Conventional example

The embodiment

Conventional example

| Total fluid volume [μL] | Sample [μL] | First reagent [μL] | Second reagent [μL] | Push water [μL] | Liquid level [mm] |
|---|---|---|---|---|---|
| 275 | 12.5 | 125 | 125 | 13 | 13.8 |
| 220 | 10.0 | 100 | 100 | 10 | 11.0 |
| 165 | 7.5 | 75 | 75 | 8 | 8.3 |
| 110 | 5.0 | 50 | 50 | 5 | 5.5 |

F I G. 12

Contact surface with test solution of test container
Magnet size: 1×5×5mm
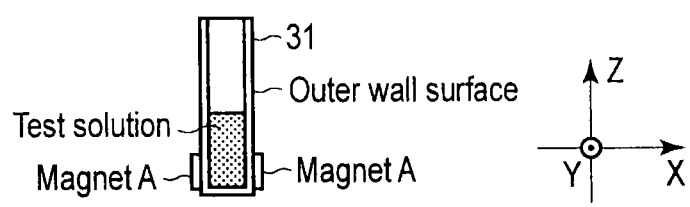
F I G. 14A
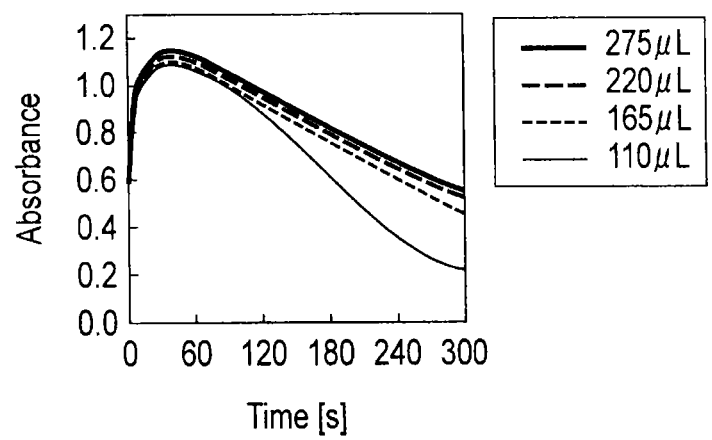
F I G. 14B Contact surface with test solution of test container
Magnet size: 1×5×10mm Geometry of the embodiment
(lower end of magnet projects downward by 4 mm from bottom surface of test container)

Photometric position A: d ≤ h
Photometric position B: d ≤ h
d = 6.2 mm

Geometry of conventional example
(lower end of magnet projects downward by 2 mm from bottom surface of test container)

Photometric position A: d > h
Photometric position B: d ≤ h
d = 6.2 mm

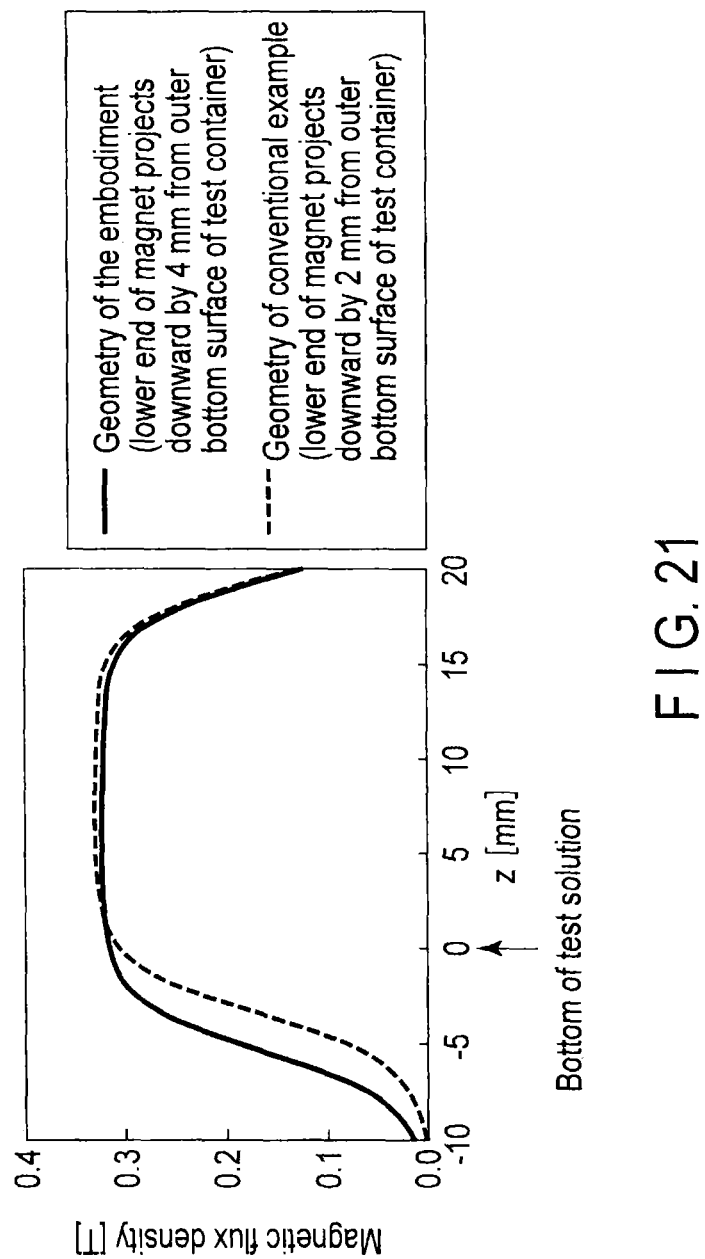
F I G. 21

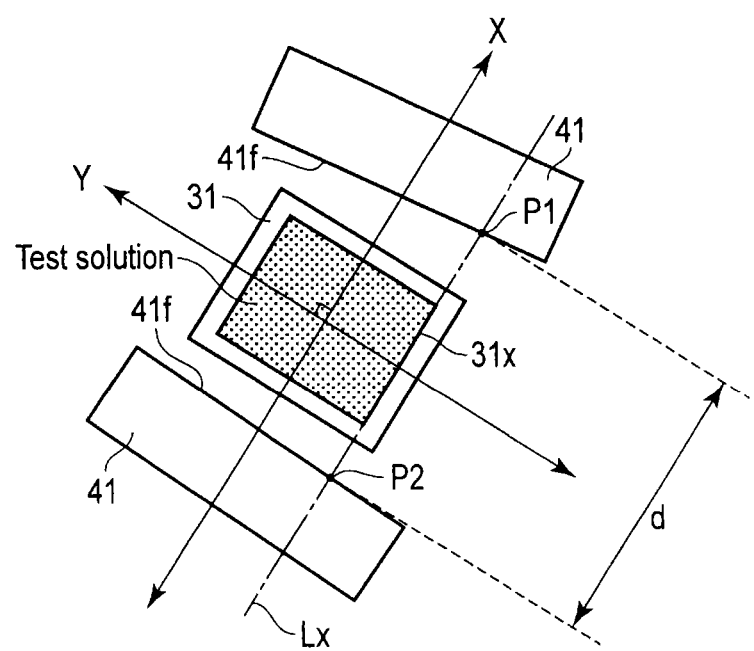
Magnet front faces 41f are nonparallel to each other
F I G. 22

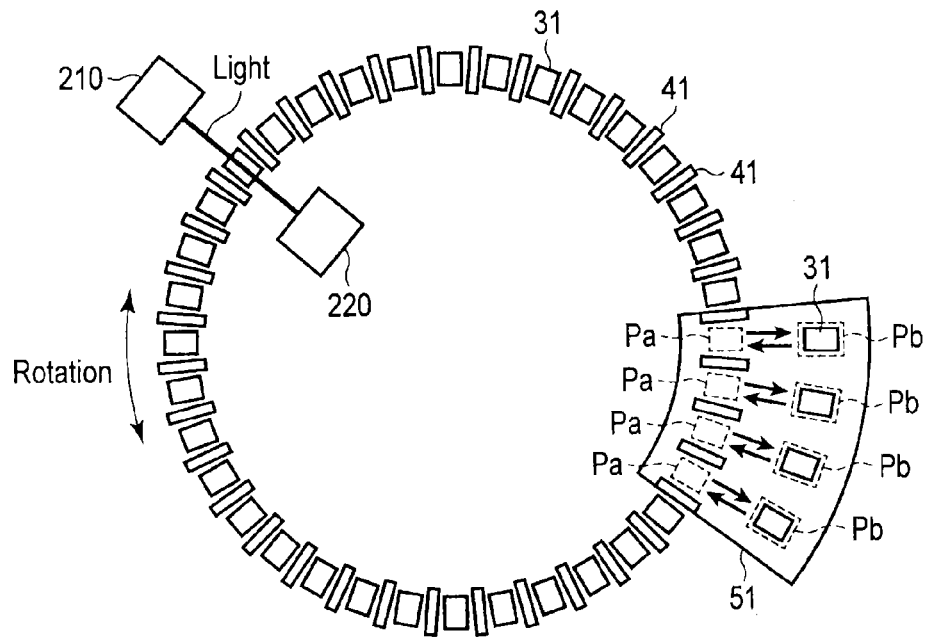
F I G. 23
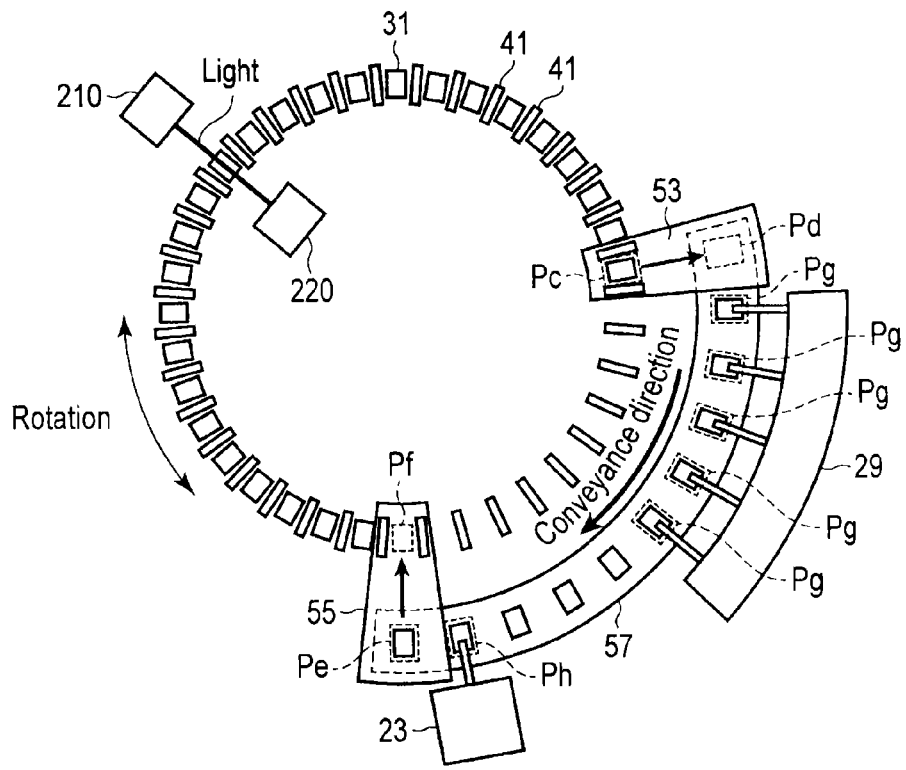
F I G. 24

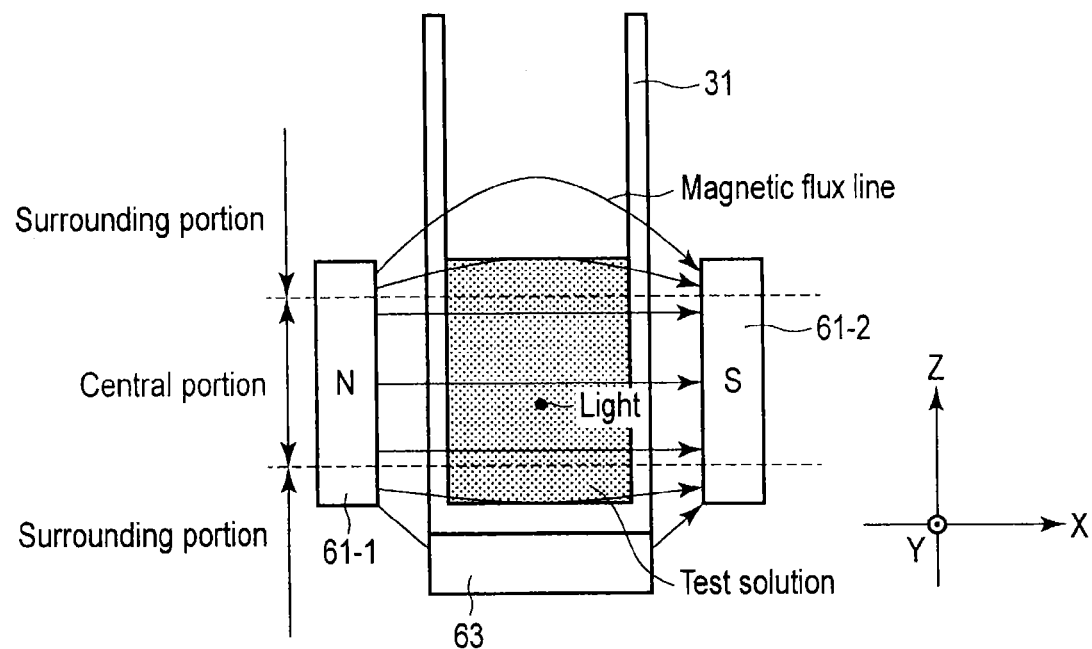
F I G. 25A
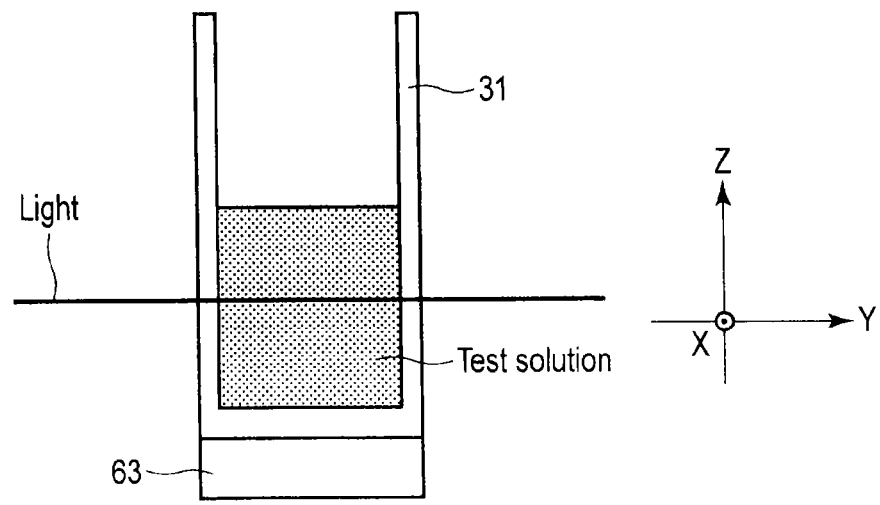
F I G. 25B

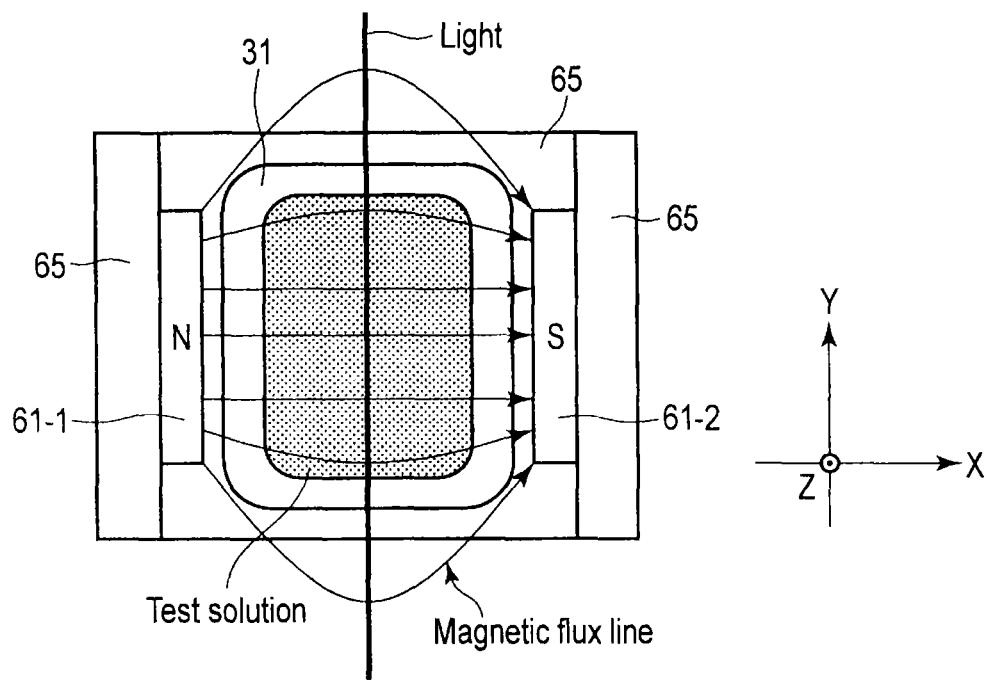
F I G. 26A
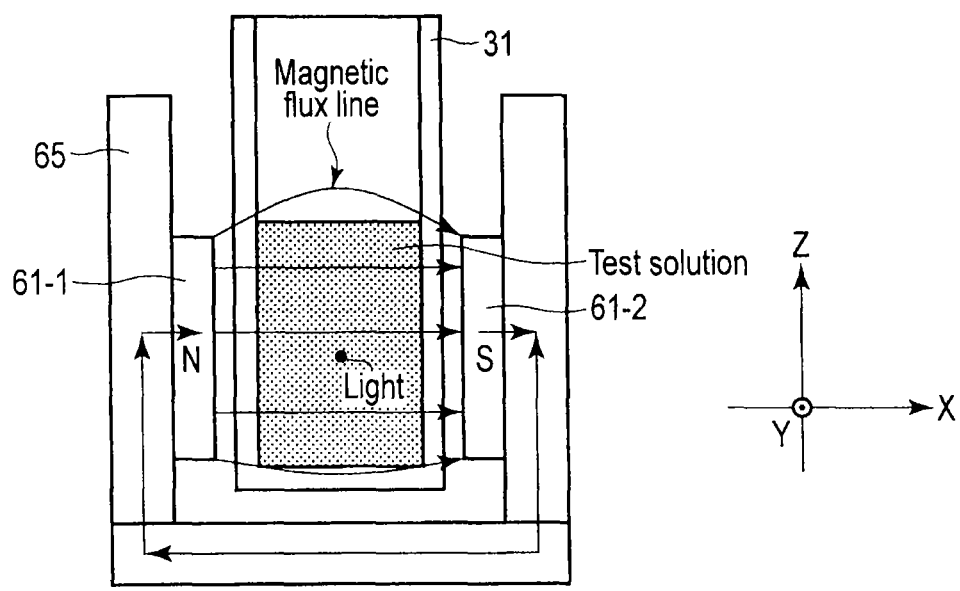
F I G. 26B

AUTOMATIC ANALYZER

CROSS-REFERENCE TO RELATED APPLICATIONS

This application is a Continuation Application of PCT Application No. PCT/JP2013/073448, filed Aug. 30, 2013 and based upon and claims the benefit of priority from the Japanese Patent Application No. 2012-192587, filed Aug. 31, 2012, the entire contents of which are incorporated herein by reference.

FIELD

Embodiments described herein relate generally to an automatic analyzer.

BACKGROUND

Magnetic particles are used in immunological tests or a sample test. By using magnetic particles, trace molecules contained in a sample can be detected selectively and highly sensitively. Magnetic particles are formed from a magnetic material such as magnetite together with a polymeric material when necessary in a fine particle shape of about a few tens of nm to a few μm in diameter. The surface of a magnetic particle is modified by an antibody or the like to be able to specifically bind directly or indirectly to particular molecules to be detected.

For example, Jpn. Pat. Appln. KOKOKU Publication No. 63-187157 discloses a measuring method of an antigen-antibody reaction using magnetic latex. According to the measuring method of Jpn. Pat. Appln. KOKOKU Publication No. 63-187157, an antibody caused to be carried by magnetic latex and an antigen present in a liquid solvent are allowed to react in the liquid solvent. After the reaction, a magnetic field is applied to the liquid solvent to recover the magnetic latex. Next, eluent is added to the recovered magnetic latex to elute antigens having reacted with antibodies carried by the magnetic latex. Then, the magnetic latex is collected by applying a magnetic field to the eluate to separate the eluate containing eluted antigens from the magnetic latex. Then, insoluble carrier particles carrying antibodies are dispensed into the separated eluate to allow a reaction and the degree of aggregation of the reaction mixture is optically measured.

Jpn. Pat. Appln. KOKAI Publication No. 1-193647 discloses a measuring method of antigens. According to the measuring method of Jpn. Pat. Appln. KOKAI Publication No. 1-193647, insoluble carrier particles containing a magnetic substance and insoluble carrier particles containing no magnetic substance are each caused to carry antibodies. These two kinds of particles are allowed to react with antigens in a liquid. After the reaction, a magnetic field is applied to the reaction mixture to collect insoluble carrier particles containing a magnetic substance in a position of a container where light measurement is not blocked. Then, antigens are measured by detecting insoluble carrier particles containing no magnetic substance floating in the liquid based on the absorbance or scattered light.

As shown in the above examples, magnetic particles can be recovered by a magnetic force by providing a magnetic field applying means such as a magnet outside and applying a magnetic field. As a result, molecules to be detected that are bonded to magnetic particles can be separated from various kinds of impurities contained in the sample and unreacted excessive reagents. With the above action, molecules to be detected can be detected and determined selectively and highly sensitively.

Apparatuses into which magnets to apply a magnetic field or the like are incorporated have been developed as analyzers that separate molecules to be detected by using magnetic particles to detect and determine such molecules.

For example, Jpn. Pat. Appln. KOKAI Publication No. 6-213900 discloses a determination method using a magnet. According to the determination method of Jpn. Pat. Appln. KOKAI Publication No. 6-213900, a magnet is provided in a lower portion of a cuvette and a portion of specimen components is precipitated and separated by using a magnetic force generated by the provided magnet. A precipitate generated by a precipitation reagent and magnetic particles are captured at the bottom of the cuvette by the magnet and separated from a supernatant fluid. Then, the analysis of the supernatant fluid excluding the precipitate and magnetic particles is carried out.

Jpn. Pat. Appln. KOKAI Publication No. 6-160401 and Jpn. Pat. Appln. KOKAI Publication No. 7-318559 disclose an immunochemical measuring apparatus. The immunochemical measuring apparatus according to Jpn. Pat. Appln. KOKAI Publication No. 6-160401 and Jpn. Pat. Appln. KOKAI Publication No. 7-318559 is removably provided with movable magnets between cuvettes attached to the entire periphery of a rotary table. Movable magnets are inserted between cuvettes when a detection target is precipitated and separated by magnetic particles and movable magnets are removed when a detection target is not precipitated and separated.

On the other hand, WO 2008/001868 discloses a method of detecting and determining molecules to be detected by using magnetic particles. In the measuring method according to WO 2008/001868, magnetic particles are caused to selectively bind to molecules to be detected that are contained in a sample and a magnetic force is added thereto to optically measure turbidity of the mixture. Then, based on the measured turbidity, the amount of molecules to be detected is calculated. In Patent Literatures 1 and 2, magnetic particles are a means for separating antibodies and are not directly involved in optical measurement. The determination method according to WO 2008/001868 is different from the above one. That is, in the determination method according to WO 2008/001868, molecules to be detected are optically detected and thus, optical properties derived directly from magnetic particles can be measured. According to this method, special reagents such as pigments to optically detect molecules to be detected are not needed and separation and cleaning processes are simplified and therefore, the time needed for inspection is shortened.

As an example of providing a magnet that forms a magnetic field for an inspection apparatus that optically detects coloring derived from magnetic particles, WO 2008/001868 shows a configuration in which a small neodymium magnet is arranged on the side face of a cell for a spectrophotometer. Jpn. Pat. Appln. KOKAI Publication No. 2009-168636 shows an example in which a magnetic field forming means is provided in an area excluding the neighborhood of a moving path of an inspection apparatus and a removal position of an object inside a cuvette. A cleaning mechanism is arranged in the removal position. The magnetic field forming means is not provided near the removal position in order to make cleaning more efficient by preventing magnetic particles from being fixed to the side wall of a cuvette by a magnetic force. Jpn. Pat. Appln. KOKAI Publication No. 2009-168636 also shows an example in which the magnetic field forming means is arranged at predetermined intervals in a magnetic field and an example in which the magnetic field forming means is provided on the side wall of a moving path at the substantially the same height as that of an optical path.

In Patent Literatures 1 and 2, the main purpose of using magnetic particles is to separate impurities and excessive reagents contained in a test solution from molecules to be detected. In this case, a magnetic field applying means only needs to be able to provide enough magnetic field strength and an appropriate magnetic field gradient to the test solution so that the separation operation is completed within a predetermined time and many variations of the concrete structure of the magnetic field applying means and the arrangement thereof are permitted. To be concrete, as the magnetic field applying means, for example, magnets having an appropriate magnetic force are arranged close to each other on the side face or at the bottom of a cuvette to aggregate magnetic particles to be separated in a narrow range of the side wall of the container. As a result, the subsequent cleaning process to remove impurities is made more efficient. Thus, the magnet is formed in a size substantially the same as or smaller than a contact portion with the test solution of the side face of the cuvette. Similarly, in Patent Literatures 3, 4, and 5, the area of one surface of a magnet facing a cuvette is smaller than the contact surface with the test solution of the side face of the cuvette. If the purpose is to separate molecules to be detected by magnetic particles, the purpose can adequately be achieved by the above magnetic field applying means.

However, the aforementioned conventional magnetic field applying means is insufficient for the determination method as disclosed in WO 2008/001868 in which molecules to be detected are determined by optically measuring turbidity or absorbance of the test solution derived directly from magnetic particles directly or indirectly bound to molecules to be detected.

That is, when magnetic particles are injected into a sample or reagent contained in a cuvette, normally the test solution is stirred by a predetermined method immediately after the injection of magnetic particles to obtain an inspection result of excellent reproducibility by promoting a reaction between the sample and reagent. Immediately after the stirring, the concentration of magnetic particles in the test solution is spatially uniformly distributed. However, if a magnetic field is applied to the test solution after stirring by a conventional magnetic field applying means, the distribution of the magnetic field in the test solution is distorted even if a magnet is installed below the bottom of the cuvette or even if a magnet is installed on the side face of the cuvette. The concentration distribution of magnetic particles becomes more spatially non-uniform resulting from the distortion of the magnetic field distribution with the passage of time. Non-uniformity in the concentration distribution of magnetic particles leads to fluctuations of measured values of absorbance or turbidity in the determination method disclosed in WO 2008/001868.

If the concentration of magnetic particles becomes non-uniform due to a magnetic field, more specifically, problems as described below arise.

When turbidity or absorbance derived from magnetic particles is optically measured, measurement results are different in accordance with the passing location of a measuring beam in the cuvette or test solution if the concentration distribution of magnetic particles becomes non-uniform. In addition, it becomes necessary to change the inspection reagent or reaction conditions for different detection targets and thus, the fluid volume of the test solution may change from inspection item to inspection item. Non-uniformity in the concentration distribution of magnetic particles adversely affects measurement results only if the fluid volume of test solution changes even if the mixing ratio of magnetic particles is constant. Thus, each time measurement conditions or the configuration of the inspection apparatus is changed, a complicated procedure like redesigning the reagent or reaction conditions is needed to obtain appropriate measurement results. Accordingly, the cost to develop an automatic analyzer increases or the inspection time increases.

When magnetic particles and other reagents or samples are allowed to react in a magnetic field, an area in which the reaction is promoted and an area in which the reaction is less likely to occur are mixed in the test solution caused by non-uniformity in the concentration distribution of magnetic particles, leading to lower reproducibility of inspection results or an occurrence of fluctuations.

Further, while fluctuations in relative physical relationship between the test solution and the magnetic field applying means arises due to producing tolerances of the size of the cuvette or a fixing means, if a magnetic field that makes the concentration distribution of magnetic particles non-uniform is applied, inspection results vary from cuvette to cuvette due to shifting of the relative physical relationship between the test solution and the magnetic field applying means.

WO 2008/001868 shows the configuration in which a small neodymium magnet is installed on the side face of a cell for a spectrophotometer. In this example, the magnetic flux density decreases from the center toward the peripheral edge portion of the magnet with swelling lines of magnetic force to the outer side and thus, magnetic particles present in an area close to edges of the magnet in the test solution move from the outer side toward the inner side. Thus, different results of the temporal change curve of turbidity of the test solution are obtained depending on the photometry position. In addition, if the fluid volume of the test solution is different, the number of magnetic particles moving from the outer side toward the inner side changes and thus, inspection results are also considered to be affected by the fluid volume.

Jpn. Pat. Appln. KOKAI Publication No. 2009-168636 discloses an example in which a magnetic field applying means is installed under a cuvette along a moving path of the cuvette. In this case, while the magnetic flux density is high near the bottom of the test solution, the magnetic field rapidly decreases upward from the bottom of the test solution. Thus, while magnetic particles near the bottom of the test solution are quickly attracted to the bottom of the cuvette, only a weak magnetic force acts on magnetic particles in an upper portion of the test solution and the concentration of magnetic particles becomes non-uniform in an up and down direction of the cuvette. Therefore, if the photometry position or the fluid volume of the test solution changes, measurement results are affected. In addition, in Jpn. Pat. Appln. KOKAI Publication No. 2009-168636, no magnetic field applying means is provided in an area where a cleaning mechanism to remove reactants is present and the magnetic field distribution is significantly distorted in this area and thus, when the cuvette pass through this area, the concentration distribution of magnetic particles is expected to change in a complex manner, adversely affecting measurement results.

An object of an embodiment is to obtain high-precision inspection results from an automatic analyzer that determines molecules to be detected by optically measuring turbidity or absorbance of a test solution derived directly from magnetic particles.

BRIEF DESCRIPTION OF THE DRAWINGS

FIG. 2 is a diagram showing an arrangement example of cuvettes and magnets in a reaction disk in FIG. 1;

FIG. 3 is a diagram schematically showing a physical relationship of a photometric mechanism in FIG. 1, the cuvette, and the magnet;

FIG. 12 is a diagram showing a table of the fluid volume of a sample, the fluid volume of a first reagent, the fluid volume of a second reagent, the fluid volume of intruding water, and the height of the liquid for each total fluid volume of four stages of the test solution used for a preliminary measurement test of temporal changes of absorbance in the present embodiment;

FIG. 14A is a diagram showing an arrangement example of the magnet A (X direction length×Y direction length×Z direction length=1×5×5 mm) on an outer wall surface opposite to a contact surface of the test solution of the cuvette;

FIG. 14B is a diagram showing temporal change curves of absorbance for each total fluid volume of the test solution in FIG. 12 for the arrangement in FIG. 14A;

FIG. 21 is a diagram showing a graph showing distributions at X=0, Y=0 along the Z direction of the magnetic flux densities in the X direction in the geometrical arrangement according to the present embodiment and the geometrical arrangement according to the comparative example in FIG. 20 by superimposing both distributions;

FIG. 22 is a diagram showing the geometrical arrangement of the two magnets according to the present embodiment when the magnet fronts of the magnets are arranged in a non-parallel manner;

FIG. 23 is a schematic plan view of a periphery of the reaction disk of the automatic analyzer according to an application example 1 of the present embodiment;

FIG. 24 is a schematic plan view of the periphery of the reaction disk of the automatic analyzer according to an application 2 of the present embodiment;

FIG. 25A is a diagram schematically showing an arrangement example of a magnet and a ferromagnetic substance (iron piece) according to a modification and a diagram of the cuvette viewed from the Y direction;

FIG. 25B is a diagram of the cuvette in FIG. 25A viewed from the X direction;

FIG. 26A is a diagram schematically showing an arrangement example of the magnet and the iron piece according to another arrangement example and a diagram of the cuvette viewed from above; and FIG. 26B is a diagram of the cuvette in FIG. 26A viewed from the Y direction.

DETAILED DESCRIPTION

In general, according to one embodiment, an automatic analyzer includes a magnetic field generator and a photometric mechanism. The magnetic field generator configured to generate a magnetic field applied to a test solution containing a sample and magnetic particles accommodated in a cuvette. The photometric mechanism configured to include a light source that irradiates light toward the test solution and a detector provided in a position opposed to the light source across the cuvette to detect the light from the test solution. The magnetic field generator has a geometrical arrangement such that a magnetic flux density of the magnetic field in the test solution inside the cuvette becomes substantially uniform.

An automatic analyzer according to the present embodiment will be described below with reference to drawings.

Figure 1:
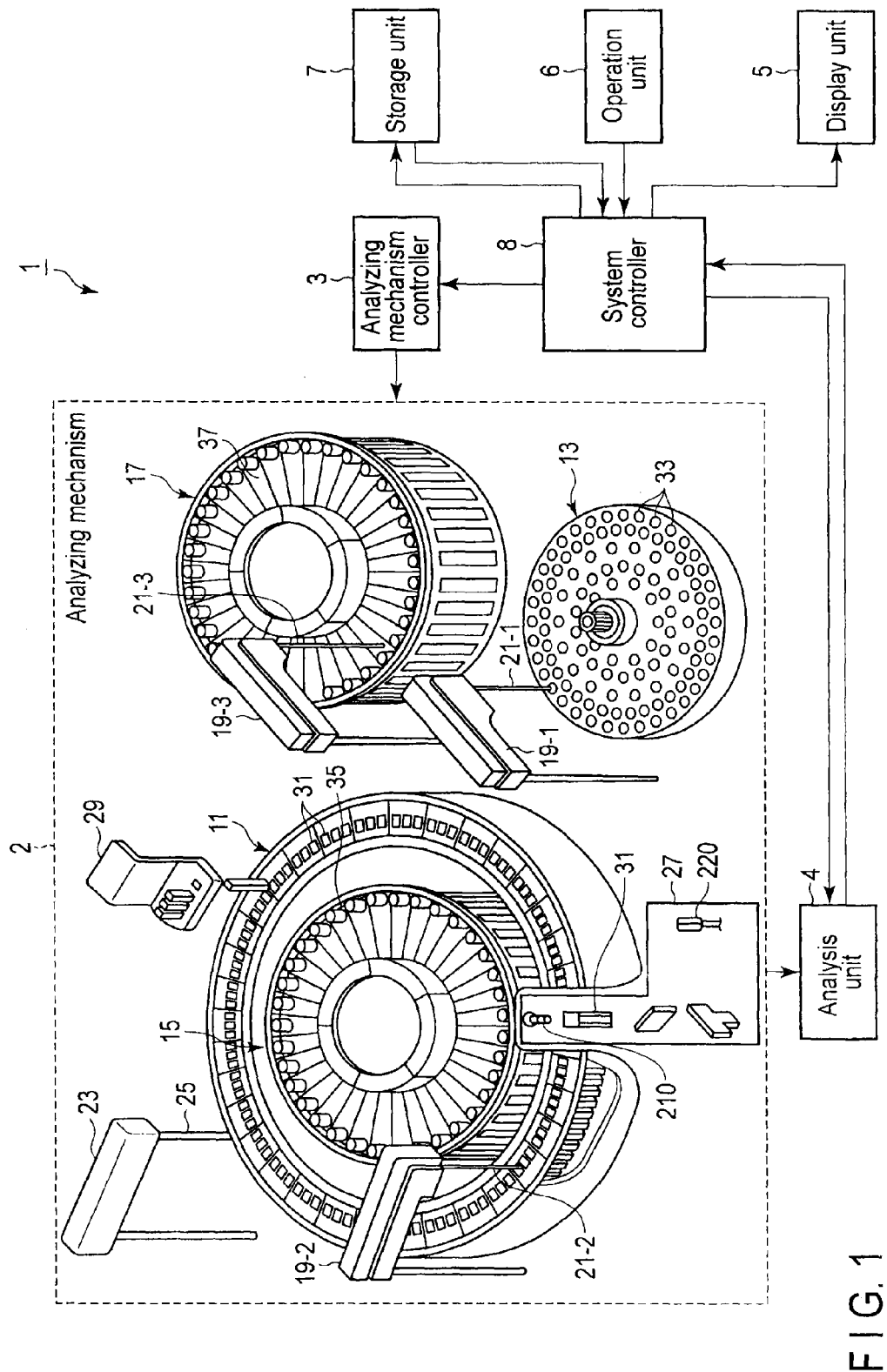
FIG. 1 is a diagram showing a configuration of an automatic analyzer according to the present embodiment.

FIG. 1 is a diagram showing the configuration of an automatic analyzer according to the present embodiment. As shown in FIG. 1, an automatic analyzer 1 includes an analysis mechanism 2, an analysis mechanism controller 3, an analysis unit 4, a display unit 5, an operation unit 6, a storage unit 7, and a system controller 8.

The analysis mechanism 2 operates according to the control of the analysis mechanism controller 3. The analysis mechanism 2 is provided in a cabinet of the automatic analyzer. The analysis mechanism 2 is mounted with, for example, as shown in FIG. 1, a reaction disk 11, sample disk 13, a first reagent repository 15, a second reagent repository 17, a sample arm 19-1, a sample probe 21-1, a first reagent arm 19-2, a first reagent probe 21-2, a second reagent arm 19-3, a second reagent probe 21-3, a stirring arm 23, a stirrer 25, a photometric mechanism 27, and a cleaning mechanism 29.

The reaction disk 11 holds a plurality of cuvettes 31 arranged on a circumference. The reaction disk 11 alternately repeats a rotation and a stop at specified time intervals. As will be described later, the reaction disk 11 is provided with magnets to apply a magnetic field to a test solution of each of the cuvettes 31. The sample disk 13 is arranged near the reaction disk 11. The sample disk 13 holds sample containers 33 in which samples are contained. The sample disk 13 rotates in such a way that the sample container 33 containing a sample to be dispensed is arranged in a sample suction position. The first reagent repository 15 holds a plurality of first reagent containers 35 in which a first reagent that selectively reacts with inspection items of a sample is contained. The first reagent repository 15 rotates in such a way that the first reagent container 35 containing the first reagent to be dispensed is arranged in a first reagent suction position. The second reagent repository 17 is arranged near the reaction disk 11. The second reagent repository 17 holds a plurality of second reagent containers 37 in which a second reagent corresponding to the first reagent is contained. The second reagent repository 17 rotates in such a way that the second reagent container 37 containing the second reagent to be dispensed is arranged in a second reagent suction position.

In the present embodiment, a solution containing magnetic particles that specifically binds directly or indirectly to molecules to be inspected that are contained in a sample is used as the first reagent or the second reagent. If magnetic particles are used when a trace quantity of molecules to be inspected is contained in a sample, molecules to be inspected can be determined and analyzed highly sensitively.

The sample arm 19-1 is arranged between the reaction disk 11 and the sample disk 13. The sample probe 21-1 is attached to the tip of the sample arm 19-1. The sample arm 19-1 vertically movably supports the sample probe 21-1. In addition, the sample arm 19-1 supports the sample probe 21-1 rotatably along a circular rotation locus. The rotation locus of the sample probe 21-1 passes through the sample suction position on the sample disk 13 and a sample discharge position on the reaction disk 11. The sample probe 21-1 takes in a sample from the sample container 33 arranged in the sample suction position on the sample disk 13 and discharges the sample to the cuvette 31 arranged in the sample discharge position on the reaction disk 11.

The first reagent arm 19-2 is arranged near the outer circumference of the reaction disk 11. The first reagent probe 21-2 is attached to the tip of the first reagent arm 19-2. The first reagent arm 19-2 vertically movably supports the first reagent probe 21-2. In addition, the first reagent arm 19-2 supports the first reagent probe 21-2 rotatably along a circular rotation locus. The rotation locus of the first reagent probe 21-2 passes through the first reagent suction position on the first reagent repository 15 and a first reagent discharge position on the reaction disk 11. The first reagent probe 21-2 takes in a first reagent from the first reagent container 35 arranged in the first reagent suction position on the first reagent repository 15 and discharges the first reagent to the cuvette 31 arranged in the first reagent discharge position on the reaction disk 11.

The second reagent arm 19-3 is arranged between the reaction disk 11 and the second reagent repository 17. The second reagent probe 21-3 is attached to the tip of the second reagent arm 19-3. The second reagent arm 19-3 vertically movably supports the second reagent probe 21-3. In addition, the second reagent arm 19-3 supports the second reagent probe 21-3 rotatably along a circular rotation locus. The rotation locus of the second reagent probe 21-3 passes through the second reagent suction position on the second reagent repository 17 and a second reagent discharge position on the reaction disk 11. The second reagent probe 21-3 takes in a second reagent from the second reagent container 37 arranged in the second reagent suction position on the second reagent repository 17 and discharges the second reagent to the cuvette 31 arranged in the second reagent discharge position on the reaction disk 11.

The stirring arm 23 is arranged near the outer circumference of the reaction disk 11. The stirrer 25 is attached to the tip of the stirring arm 23. The stirring arm 23 vertically movably supports the stirrer 25. In addition, the stirring arm 23 supports the stirrer 25 rotatably along a circular rotation locus. The stirrer 25 stirs a mixed solution of a sample and the first reagent or a mixed solution of a sample, the first reagent, and the second reagent in the cuvette 31 arranged in a stirring position on the reaction disk 11. Hereinafter, such a mixed solution will be called a test solution.

As shown in FIG. 1, the photometric mechanism 27 is provided near the reaction disk 11. The photometric mechanism 27 operates according to the control of the analysis mechanism controller 3. To be concrete, the photometric mechanism 27 includes a light source 210 and a detector 220. The light source 210 irradiates the test solution in the cuvette 31 in the photometry position on the reaction disk 11 with light. The detector 220 is arranged in a position opposed to the light source across the cuvette 31 in the photometry position. The detector 220 detects light irradiated from the light source and having passed through the cuvette 31 and the test solution, light reflected by the cuvette 31 or the test solution, or light scattered by the cuvette 31 or the test solution. The detector 220 generates data having measured values in accordance with intensity of the detected light (hereinafter, called photometric data). The generated photometric data is supplied to the analysis unit 4.

The cleaning mechanism 29 is provided on the outer circumference of the reaction disk 11. The cleaning mechanism 29 operates according to the control of the analysis mechanism controller 3. To be concrete, the cleaning mechanism 29 has a cleaning nozzle and a drying nozzle mounted thereon. The cleaning mechanism 29 cleans the cuvette 31 in a cleaning position of the reaction disk 11 by the cleaning nozzle and dries the cuvette by the drying nozzle.

The analysis mechanism controller 3 operates each apparatus and mechanism in the analysis mechanism 2 according to the control of the system controller 8. The analysis unit 4 calculates absorbance of the test solution derived directly from magnetic particles based on photometric data or calculates turbidity based on the calculated absorbance. The analysis unit 4 also determines and analyzes molecules to be detected in accordance with the inspection item based on the calculated turbidity or absorbance of the test solution. The display unit 5 includes a display device, for example, a CRT display, a liquid crystal display, an organic EL display, or a plasma display. The display unit 5 displays analysis results by the analysis unit. The operation unit 6 accepts various instructions and information input from an operator via an input device. As the input device, a pointing device such as a mouse and track ball, a selection device such as a switch button, or an input device such as a keyboard can appropriately be used. The storage unit 7 stores an operation program of the automatic analyzer 1 and the like. The system controller 8 functions as the center of the automatic analyzer 1. The system controller 8 reads the operation program from the storage unit 7 and controls each unit 3, 4, 5, 7 according to the operation program.

Hereinafter, the automatic analyzer 1 according to the present embodiment will be described in detail.

The automatic analyzer 1 according to the present embodiment has magnets to apply a magnetic field to the test solution in the cuvette 31. The magnets according to the present embodiment have a geometrical arrangement (geometry) such that the magnetic flux density of a magnetic field is substantially uniform over the entire test solution in the cuvette 31.

FIG. 2 is a diagram schematically showing an arrangement example of the cuvettes 31 and magnets 41 on the reaction disk 11. FIG. 3 is a diagram schematically showing a physical relationship of the photometric mechanism 27, the cuvette 31, and the magnet 41. The light source 210 and the detector 220 of the photometric mechanism 27 are fixed in predetermined positions inside the cabinet of the automatic analyzer 1. Light is irradiated from the light source 210 toward the detector 220. The irradiation direction of the light is defined as the Y direction. The photometry position is provided in a predetermined position on the optical path from the light source 210 to the detector 220. The cuvette 31 is rotated by the reaction disk 11 at predetermined time intervals such that light from the light source 210 crosses substantially perpendicularly in the photometry position. The test solution in the cuvette 31 is optically measured by the photometric mechanism 27 each time the photometry position is crossed. The direction along a major axis A1 of the cuvette 31 is defined as the Z direction and the direction perpendicular to both of the Y direction and the Z direction is defined as the X direction.

As the light source 210, a halogen lamp, an LED (light-emitting diode), or a laser generator can be used. Light irradiated from the light source 210 preferably contains a light in a wavelength band capable of measuring turbidity or absorbance of the test solution. If the light source 210 is a monochromatic light source such as an LED or a laser generator, the wavelength of the irradiated monochromatic light may be contained in the wavelength band capable of measuring turbidity or absorbance of magnetic particles. If the light source 210 uses a white light source such as a halogen lamp, a wavelength discriminator such as an optical filter or a monochromator may be provided prior to the detector if necessary to improve the detection sensitivity of turbidity or absorbance of magnetic particles. The detector 220 detects light in the wavelength band capable of measuring turbidity or absorbance of the test solution and converts the intensity of the detected light into an electric signal. To be concrete, as the detector 220, a photomultiplier or photo diode, or an arrayed photomultiplier or photo diode is used. To improve the S/N ratio of detection, an optical window or a condenser may be arranged between the light source 210 and the detector 220 if necessary.

The cuvette 31 is a container to contain a test solution. The cuvettes 31 are arranged in a circular shape on the reaction disk 11 with predetermined pitches. At least an incidence plane and an emission plane of planes of the cuvette 31 may be optically transparent and smooth such that optical measurements can be made by the photometric mechanism 27. In addition, the cuvette 31 may be formed from a material that is resistant to corrosion or contamination by samples, reagents, and cleaning fluids. To be concrete, the cuvette 31 may be formed from optical glass or transparent resin.

The magnets 41 are provided on the reaction disk 11 to apply a magnetic field to the test solution in the cuvette 31. The magnets 41 have a geometrical arrangement such that the magnetic flux density of the magnetic field in the test solution inside the cuvette 31 is substantially uniform. The geometrical arrangement in the present embodiment means the size and shape of the magnet 41, the relative physical relationship thereof to the cuvette 31, and the relative physical relationship between the magnets 41. The magnet 41 is arranged near the cuvette 31 on the reaction disk 11 such that the magnetic field is applied in the Z direction or the X direction perpendicular to the light incident direction (Y direction). For example, as shown in FIGS. 2 and 3, the two magnets 41 are arranged such that the cuvette 31 is sandwiched therebetween in the left and right direction. In this case, the two magnets 41 can apply a magnetic field along the X direction horizontally perpendicular to the Y direction. To apply a magnetic field having a good magnetic field distribution to the test solution, a pair of the magnets 41 is arranged such that a line A2 connecting centers of the magnets passes through the test solution inside the cuvette 31. However, the arrangement of the magnets 41 is not limited to the above example. For example, the two magnets 41 may be arranged such that the cuvette 31 is sandwiched therebetween in the up and down direction in order to apply a magnetic field along the Z direction vertically perpendicular to the Y direction.

Compared with a case when the magnets 41 are arranged above and below the cuvette 31, a case when the magnets 41 are arranged on the left and right sides of the cuvette 31 can reduce leakage of a magnetic field in the up and down direction of the cuvette 31. When the magnets 41 are arranged on the left and right sides of the cuvette 31, there is no need to arrange the magnet 41 above the cuvette 31 and keep the vicinity of an opening of the cuvette 31 always open. Thus, the discharge of a sample or reagent to the cuvette 31 is not prevented and the configuration of the apparatus can be simplified.

Any existing magnet can be applied as the magnet 41 according to the present embodiment. For example, as the magnet 41 according to the present embodiment, it is desirable to use a permanent magnet such as a ferrite magnet, Alnico magnet, samarium cobalt magnet, or neodymium magnet. A pair permanent magnets arranged like sandwiching the cuvette 31 are magnetized in a state in which S and N poles are opposed so that a magnetic field is applied in the X direction. In addition, a combination of a permanent magnet and another magnetic material can also be applied as the magnet 41. Further, the magnet 41 may also contain ferromagnetic substance such as a metal, alloy, oxide or the like. In this case, a portion of a pair of ferromagnetic substances is opposed across the cuvette 31 in the X direction or the Z direction. The other portion of the pair of ferromagnetic substances is connected to a permanent magnet (or an electromagnet) in a position apart from the cuvette 31. In this manner, a pair of ferromagnetic substances and a permanent magnet constitutes the magnet 41 (magnetic circuit). When a pair of ferromagnetic substances is arranged across the cuvette 31 in the X direction, a magnetic field is applied along the X direction and when a pair of ferromagnetic substance is arranged across the cuvette 31 in the Z direction, a magnetic field is applied along the Z direction. Further, the magnet 41 may contain an electromagnet. In this case, like the above ferromagnetic substance, the magnet 41 (magnetic circuit) including an electromagnet and a permanent magnet or another magnetic substance is constituted.

As described above, the magnets 41 have a geometrical arrangement such that the magnetic flux density of the magnetic field in the test solution inside the cuvette 31 is substantially uniform. Next, the geometrical arrangement will be described in detail.

Figure 4:
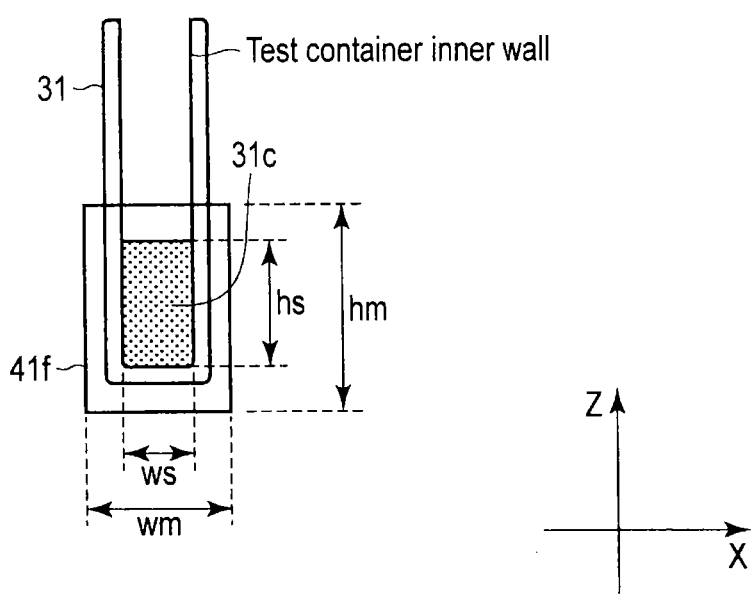
FIG. 4 is a diagram showing the cuvette and the magnet in FIG. 3 in an overlapped state.

FIG. 4 is a diagram showing the cuvette 31 and the magnet 41 in an overlapped state. It is assumed that, as shown in FIG. 4, a surface (hereinafter, called a magnet front surface) 41f opposed to the cuvette of surfaces of the magnet 41 has a width wm in the transverse direction and a length hm in the longitudinal direction. It is also assumed that a surface (hereinafter, called a test solution contact surface) 31c in contact with the test solution of the inner wall opposed to the magnet 41 of the cuvette 31 has a width ws in the transverse direction and a length hs in the longitudinal direction. The magnet 41 is formed such that the area of the magnet front surface 41f is larger than the area of the test solution contact surface 31c in order to decrease the gradient of the magnetic flux density to make the magnetic flux density flat over the entire test solution. For example, the magnet 41 is formed such that the width wm is longer than the width ws and the length hm is longer than the length hs. The magnet 41 is arranged with respect to the cuvette 31 such that when the magnet front surface 41f and the test solution contact surface 31c are overlapped, the magnet front surface 41f includes the test solution contact surface 31c.

The fluid volume of the test solution changes depending on the quantity of the sample, magnetic particles, or other reagents or changes depending on the inspection item. The test solution is contained in the cuvette 31 in a fluid volume between the minimum fluid volume and the maximum fluid volume. The maximum fluid volume is a fluid volume set to the automatic analyzer 1 and is the maximum fluid volume of the test solution that can be inspected. The minimum fluid volume is a fluid volume set to the automatic analyzer 1 and is the minimum fluid volume of the test solution that can be inspected. To avoid a case when the area of the magnet front surface 41f becomes smaller than the area of the test solution contact surface 31c depending on the liquid volume of the test solution, the width ws and the height hs may set to respective values of when the maximum liquid volume of test solution is contained in the cuvette 31.

Figure 5A:
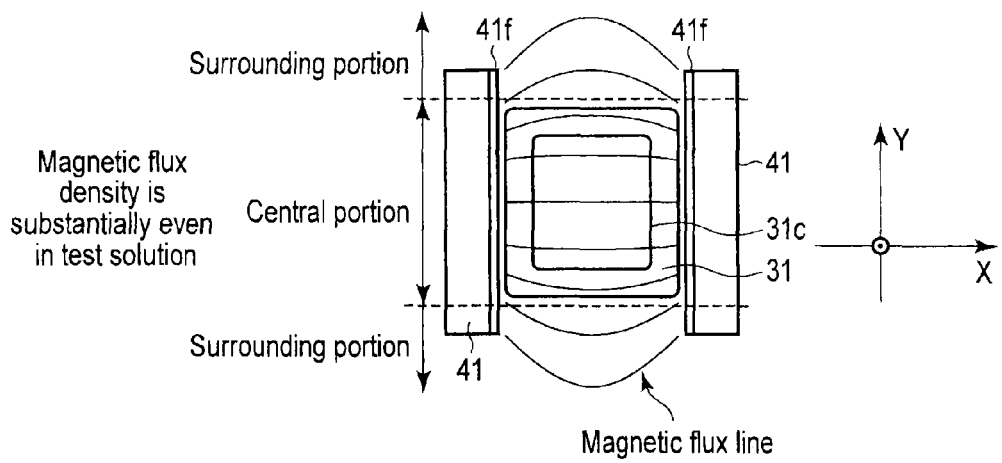
FIG. 5A is a diagram schematically showing a spatial distribution of lines of magnetic force of a magnetic field generated by the magnet according to the present embodiment.
Figure 5B:
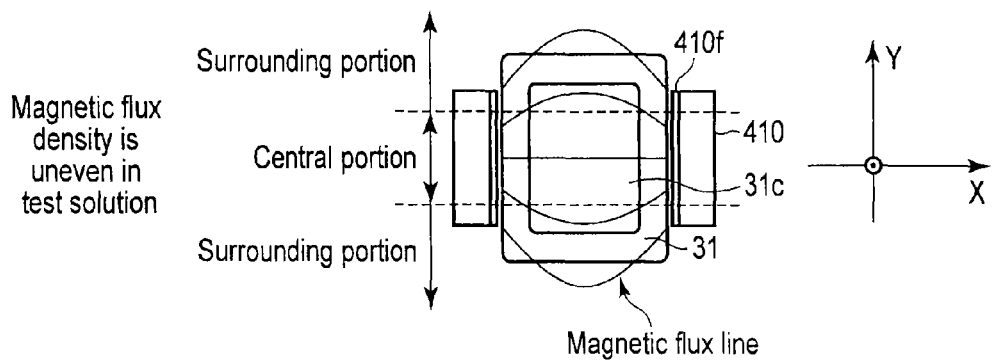
FIG. 5B is a diagram schematically showing the spatial distribution of lines of magnetic force of the magnetic field generated by a conventional magnet.

FIGS. 5A and 5B are diagrams schematically showing a spatial distribution of lines of magnetic force of a magnetic field generated by two magnets that are different in size with respect to the cuvette 31. FIGS. 5A and 5B are diagrams viewed from above the cuvette 31. FIG. 5A shows a spatial distribution of lines of magnetic force from the magnet 41 (magnet for which the magnet front surface 41f is larger than the test solution contact surface 31c) according to the present embodiment and FIG. 5B shows a spatial distribution of lines of magnetic force from a conventional magnet 410 (the magnet 410 for which a magnet front surface 410f is smaller than the test solution contact surface 31c).

The lines of magnetic force from a magnet have physical properties that are spatially more distorted in a peripheral region than in a center of the magnet. On the other hand, the magnet 41 according to the present embodiment is formed such that the magnet front surface 41f is larger than the test solution contact surface 31c of the cuvette 31 and the conventional magnet 410 has the magnet front surface 410f smaller than the test solution contact surface 31c. Therefore, compared with the magnetic flux density of a magnetic field from the magnet 410 in FIG. 5B, the magnetic flux density of a magnetic field from the magnet 41 in FIG. 5A is spatially substantially uniform over the entire test solution of the cuvette 31. Each magnet may be installed close to the cuvette to make the gradient of the magnetic flux density of a magnetic field between magnets smaller.

Figure 6:
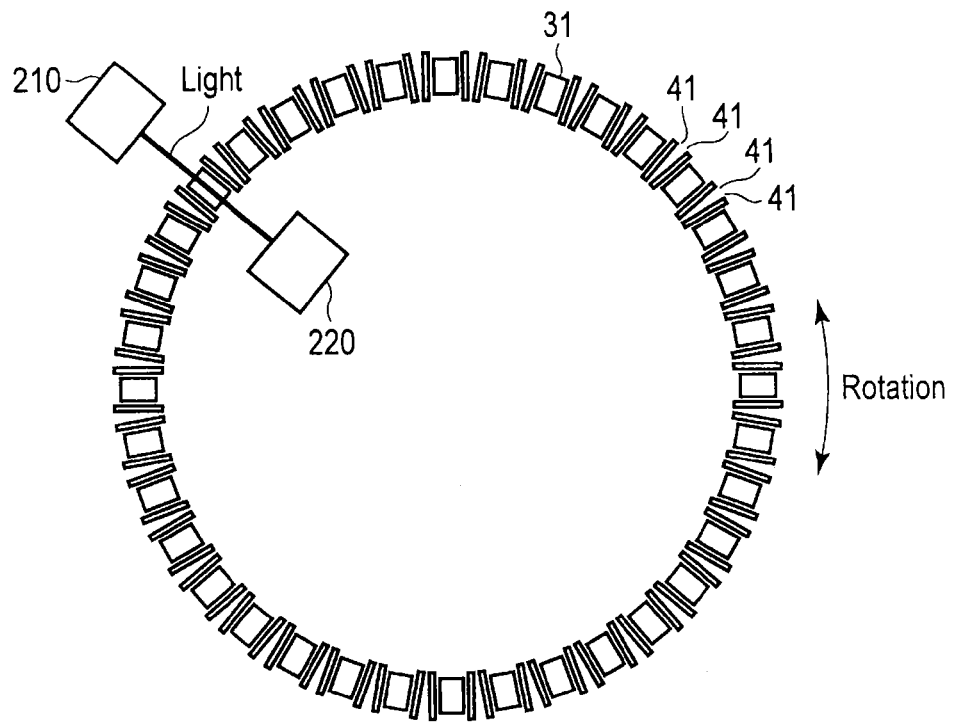
FIG. 6 is a diagram showing another arrangement example of cuvettes and magnets in the reaction disk in FIG. 1.

As shown in FIG. 2, the magnets 41 and the cuvettes 31 are alternately arranged along the circumference of the reaction disk 11. Each of the magnets 41 is polarized in the X direction toward the cuvette 31. The magnets 41 on the reaction disk 11 may all have the same magnetization direction. In the above description, the magnets 41 and the cuvettes 31 are assumed to be arranged alternately along the circumference. However, the arrangement is not limited to the above example as long as the cuvette 31 can be sandwiched between the two magnets 41. FIG. 6 is a diagram schematically showing another arrangement example of the cuvettes 31 and the magnets 41 on the reaction disk 11. As shown in FIG. 6, the two magnets 41 may be provided for one of the cuvettes 31 to sandwich each cuvette between the two magnets 41. In this case, the two magnets 41 across the cuvette 31 can be arranged in parallel and so the distortion of spatial distribution of the magnetic flux density can be reduced.

The inventors performed a simulation to verify the effect by the magnet 41 for which the magnet front surface 41f is larger than the test solution contact surface 31c. Various conditions of the simulation and simulation results will be described below.

Magnetic particles in a test solution move under the influence of a magnetic force of a magnetic field, gravity, buoyancy of the test solution, viscous resistance of the test solution and the like. Concentration distribution changes of magnetic particles in a test solution can numerically be estimated by formulating motion of magnetic particles under the action thereof and calculating positions of magnetic particles from the initial state in which the concentration distribution is uniform to a state when any time has passed. In the motion calculation of magnetic particles, property values of magnetic particles such as the diameter of magnetic particles, the ratio occupied by magnetic substance in magnetic particles, the density, specific magnetic susceptibility, and saturation magnetization, and the density and coefficient of viscosity of the test solution become parameters. These parameters are determined so as to match results of measuring concentration changes of magnetic particles by a magnetic field being actually applied by the inventors with reference to literature values. Under normal conditions, the Reynolds number Re of a test solution for motion of magnetic particles moving in the test solution is Re<1. That is, the resistance of the test solution can be represented according to the Stokes' theorem. In addition, the diameter of particles in the test solution is about 1 μm and so thermal energy and the influence of interaction between particles are ignored in the simulation.

When a magnetic field is applied to the test solution in the Z direction, if the magnetic force is sufficiently larger than gravity, the concentration distribution of magnetic particles along the Z direction is considered to change like in the X direction. For the simplification of description, the magnetic field distribution used for the simulation is set as a one-dimensional magnetic field distribution along the X direction by assuming a magnetic field applied to the test solution in the X direction. When two plate magnets are arranged by sandwiching the test solution therebetween and opposing S and N poles, the magnetic flux density distribution in the X direction inside the test solution can approximately be represented by a quadratic function of the coordinate X. In this simulation, the width of the test solution inside the cuvette along the X direction is set to 4 mm. In addition, the center concerning the X direction of the test solution inside the cuvette is set as the X coordinate 0.

Figure 7:
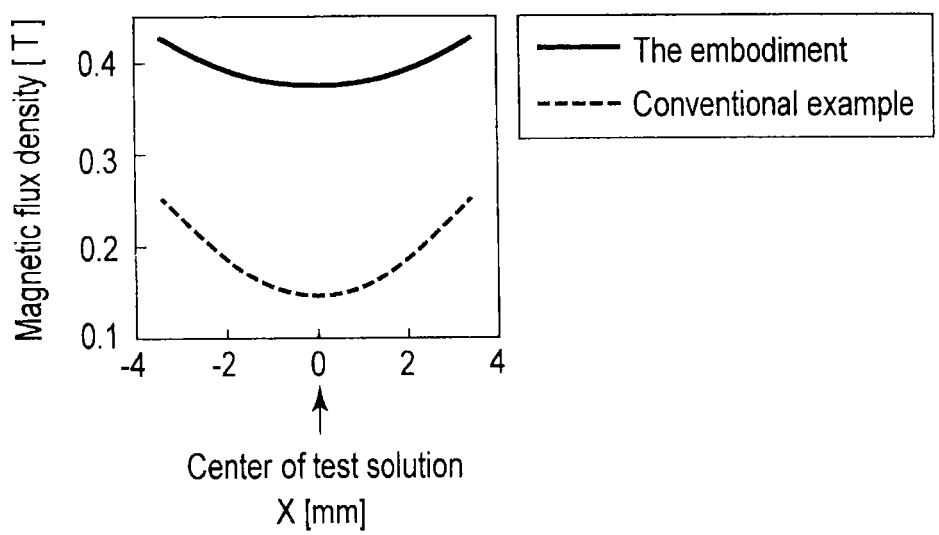
FIG. 7 is a diagram showing a graph showing distributions along the X direction of the magnetic flux densities of magnetic fields generated by the magnet according to the present embodiment and the conventional magnet by superimposing both distributions.

FIG. 7 is a diagram showing a graph showing distributions along the X direction of the magnetic flux densities [T] of magnetic fields generated by the magnet according to the present embodiment and the conventional magnet by superimposing both distributions. A dotted line in FIG. 7 shows a distribution along the X direction of the magnetic flux density [T] according to a conventional example and a solid line in FIG. 7 a distribution along the X direction of the magnetic flux density [T] according to the present embodiment. The conventional example is a case when the magnet front surface is relatively smaller than the test solution contact surface and the present embodiment is a case when the magnet front surface is relatively larger than the test solution contact surface. As shown in FIG. 7, the dent of the magnetic flux density in the center portion of the test solution along the X direction of the present embodiment is smaller than that of the conventional example. In addition, as a whole, the magnetic flux density of the present embodiment is larger than that of the conventional example. Therefore, an automatic analyzer according to the present embodiment can apply a flat magnetic flux density whose gradient along the X perpendicular to the light incident direction (Y direction) is small, by using a magnet having a relatively larger magnet front surface than the test solution contact surface, when compared with a case in which a magnet having a relatively smaller magnet front surface than the test solution contact surface.

Figure 8A:
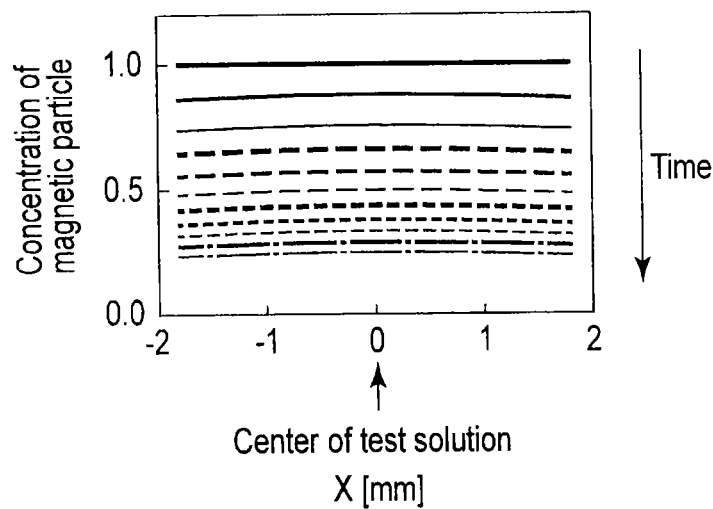
FIG. 8A is a diagram showing a graph showing temporal changes in the concentration distribution of magnetic particles in a test solution to which the magnetic field generated by the magnet according to the present embodiment is applied.
Figure 8B:
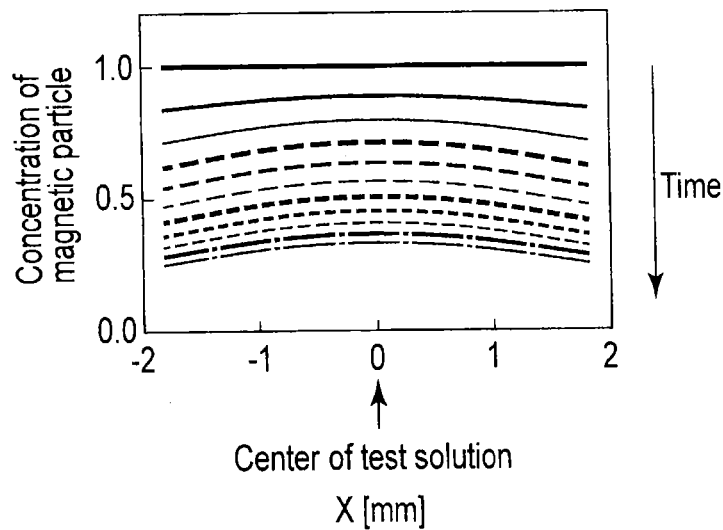
FIG. 8B is a diagram showing the graph showing temporal changes in the concentration distribution of magnetic particles in the test solution to which the magnetic field generated by the conventional magnet is applied.

FIGS. 8A and 8B are diagrams individually showing the graphs showing temporal changes in the concentration distribution of magnetic particles in the test solution to which magnetic fields generated by the magnet according to the present embodiment and the conventional magnet are applied. The graph in FIG. 8A shows temporal changes in the concentration distribution according to the present embodiment and the graph in FIG. 8B shows temporal changes of the conventional concentration distribution. In FIGS. 8A and 8B, it is assumed that magnetic particles are initially distributed uniformly in the test solution. The concentration of magnetic particles in the test solution is normalized by using the concentration in the initial state. The concentration distribution is calculated every 30 seconds and the concentration distribution at every time is represented by a different type of line. Because magnetic particles are sucked onto the wall surface of the cuvette by a magnetic force, the concentration decreases with the passage of time as a whole. Incidentally, magnetic particles adsorbed on the wall surface are not taken into consideration in the calculation.

In the case of the conventional example in which a magnetic field is applied by a magnet having a relatively smaller magnet front surface than the test solution contact surface, as shown in FIG. 8B, the lowering speed of concentration is slower in the center of the test solution than near the inner wall and thus, the concentration distribution of magnetic particles is found to become more non-uniform with the passage of time. The inventors performed similar calculations by changing the gradient of the magnetic flux density of the magnetic field distribution. As a result, the fact that the concentration distribution of magnetic particles becomes more non-uniform with an increasing gradient of the magnetic flux density was found. The magnetic force acting on magnetic particles is proportional to the product of the magnetic flux density and the gradient of the magnetic flux density in the position of magnetic particles. Both of the magnetic flux density and the gradient of the magnetic flux density in the center of the test solution are smaller than those near the inner wall and thus, the magnetic force is smaller in the center of the test solution than near the inner wall. In the distribution in which, like the conventional magnetic field distribution, the magnetic flux density in the center of the test solution is significantly dented, the difference of the magnetic forces in the center of the test solution and near the inner wall of the cuvette increases and so the decrease in concentration near the inner wall is faster, leading to a non-uniform concentration distribution.

In the case of the present embodiment in which, as shown in FIG. 8A, a magnetic field is applied by the magnet 41 having the magnet front surface 41f relatively larger than the test solution contact surface 31c, the amount of decrease of the magnetic flux density in the center of the test solution is smaller. To attract magnetic particles at about the same speed as in the conventional magnetic field distribution, a magnetic field in which the magnetic flux density is high and the gradient is small may be applied.

Accordingly, the difference of magnetic forces acting on magnetic particles in the center of the test solution and near the inner wall of the cuvette 31 becomes smaller and the lowering speed of concentration with the passage of time becomes uniform regardless of the position in the test solution. As shown in FIG. 8A, by using the magnet 41 having the magnet front surface 41f larger than the test solution contact surface 31c, though the concentration as a whole decreases with the passage of time, it becomes possible to make the concentration value along the X direction at each time can be made substantially constant and maintain the concentration distribution of magnetic particles substantially uniform over the entire test solution.

The inventors performed similar calculations by changing property values such as the diameter of magnetic particles, the ratio occupied by magnetic substance in magnetic particles, and the coefficient of viscosity of the test solution. The inventors found that though the degree of temporal changes of the concentration of magnetic particles changes in accordance with these property values, uniformity in the concentration distribution of magnetic particles generally does not change in accordance with these property values. That is, by applying a magnetic field to the test solution using the magnet 41 having the magnet front surface 41f larger than the test solution contact surface 31c, uniformity in the concentration distribution of magnetic particles is improved and, as a result, variations of measured values such as absorbance and turbidity of the test solution in accordance with the spatial position of the incident light can be reduced.

The relative physical relationship between the cuvette 31 and the magnet 41 may be shifted due to variations of the size and installation position of the cuvette 31. The inventors performed a simulation of temporal changes in the concentration distribution of magnetic particles when the relative position between the cuvette 31 and the magnet 41 is shifted in the X direction.

Figure 9A:
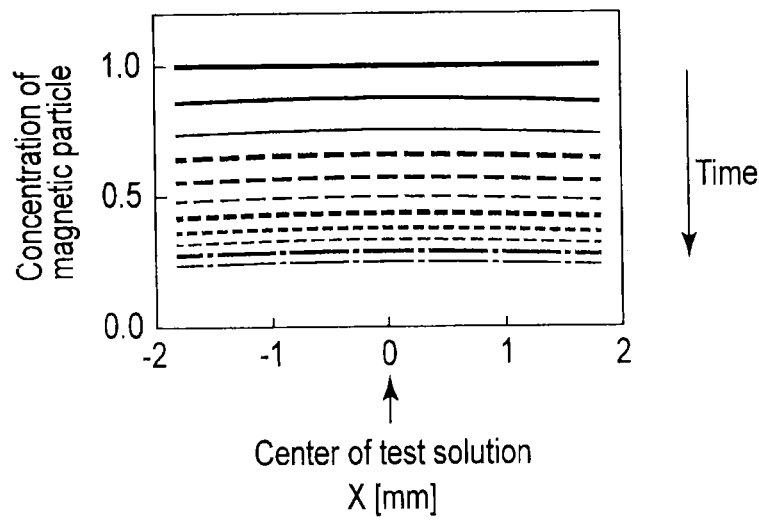
FIG. 9A is a diagram showing the graph showing temporal changes in the concentration distribution of magnetic particles in the test solution to which the magnetic field generated by the magnet according to the present embodiment is applied when the cuvette is shifted in the X direction by 0.4 mm.
Figure 9B:
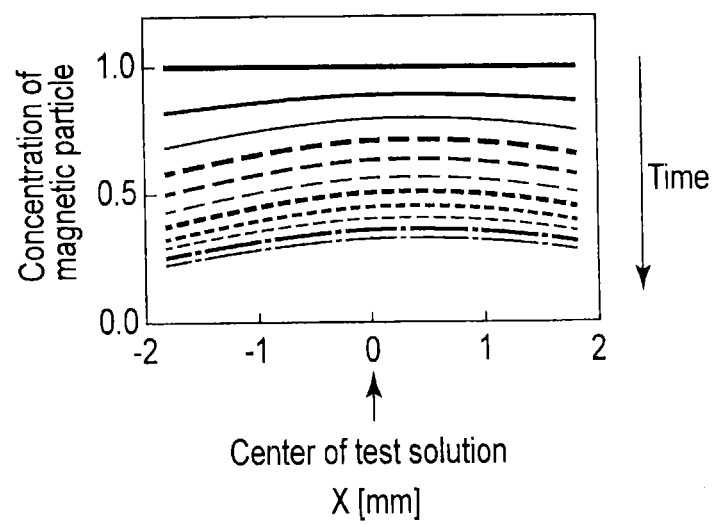
FIG. 9B is a diagram showing the graph showing temporal changes in the concentration distribution of magnetic particles in the test solution to which the magnetic field generated by the conventional magnet is applied when the cuvette is shifted in the X direction by 0.4 mm.

FIGS. 9A and 9B are diagrams individually showing the graphs showing temporal changes in the concentration distribution of magnetic particles in the test solution to which magnetic fields generated by the magnet 41 according to the present embodiment and the conventional magnet are applied when the cuvette 31 is shifted in the X direction by 0.4 mm. The graph in FIG. 9A shows temporal changes in the concentration distribution according to the present embodiment and the graph in FIG. 9B shows temporal changes of the conventional concentration distribution. In the conventional magnetic field distribution, as shown in FIG. 9B, non-uniformity in the concentration distribution of magnetic particles increases with an increasing lateral shift of the cuvette 31 from the center of the magnetic field distribution. As a result, in the case of the conventional example, variations of measurement results increase with an increasing distance of the cuvette 31 from the center of the magnetic field distribution. In the magnetic field distribution according to the present embodiment, by contrast, as shown in FIG. 9A, even if the cuvette 31 is laterally shifted from the center of the magnetic field distribution, uniformity in the concentration distribution of magnetic particles can be maintained. That is, when the magnet 41 having the magnet front surface 41f relatively larger than the test solution contact surface 31c is used, non-uniformity in the concentration distribution resulting from relative position shifts between the cuvette 31 and the magnet 41 and variations of measured values accompanying the non-uniformity can be reduced when compared with a case in which a magnet having a magnet front surface relatively smaller than a test solution contact surface is used.

The magnetic force acting on magnetic particles is proportional, as described above, to the product of the magnetic flux density and the gradient of the magnetic flux density in the position of magnetic particles. Therefore, the magnetic force becomes weaker with a decreasing gradient of the magnetic flux density to maintain uniformity in the concentration distribution and the speed of concentration change slows down, leading to a longer inspection time. It is necessary to increase the magnetic flux density to swiftly complete a sample inspection. The inventors performed a simulation of the concentration distribution of magnetic particles in the test solution by changing the magnetic flux density. Based on the simulation, the inventors found that sufficiently high magnetic flux densities can be maintained in regions other than a region on the X axis by setting the magnetic flux density [T] on the X axis passing the center of opposed magnets to 0.1 T or more and the concentration can be changed in a short time while maintaining uniformity in the concentration distribution of magnetic particles in the test solution. Therefore, the magnet 41 according to the present embodiment may be configured and arranged so as to be able to apply a magnetic field whose magnetic flux density [T] is 0.1 T or more. Accordingly, the automatic analyzer 1 according to the present embodiment can reduce the inspection time.

The magnetic field to be applied to the test solution can be calculated based on a simulation in which various magnetic field distributions are calculated by changing the magnetic flux density and the gradient of the magnetic flux density. The inventors performed a simulation of the concentration distribution of magnetic particles by changing the magnetic flux density and the gradient of the magnetic flux density. As a result of the simulation, the inventors verified the tendency that uniformity in the concentration distribution increases with a decreasing gradient of the magnetic flux density and conversely, non-uniformity in the concentration distribution of magnetic particles increases with an increasing gradient of the magnetic flux density. Also based on the simulation, the inventors found that the gradient of the magnetic flux density can be reduced also in a region outside the X axis and uniformity in the concentration distribution in the test solution can be maintained at a high level by limiting fluctuations of the magnetic flux density on the X axis passing the center of the opposed magnets to 0.04 T/mm or less. Therefore, the magnet 41 according to the present embodiment may be configured and arranged so as to be able to apply a magnetic field whose fluctuations [T/mm] of the magnetic flux density along the X direction is 0.04 T/mm or less. Accordingly, the automatic analyzer 1 according to the present embodiment can reduce variations of measurement by maintaining uniformity in the concentration distribution of magnetic particles.

Next, changes in the magnetic field distribution in accordance with differences in size and shape of the magnet will be described. The inventors calculated magnetic field distributions by a plurality of magnets having different sizes and shapes. A rectangular neodymium magnet (NeoMag Co., Ltd., material: N48M, thickness: 3.0 mm) is used as the magnet and two rectangular neodymium magnets are installed by opposing S and N poles across the cuvette 31. The distance between the rectangular neodymium magnets is set to 6 mm. As the cuvette 31, a rectangular glass cell in which the width in the X direction is 6 mm and the width in the Y direction is 7 mm is used. The thickness of glass of the glass cell is set to 1 mm. Therefore, a test solution in the glass cell has the X-direction width of 4 mm and the Y-direction width of 5 mm.

Figure 10A:
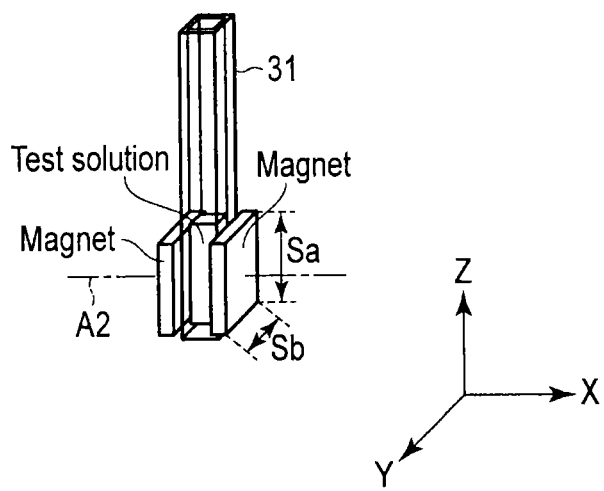
FIG. 10A is a diagram showing calculation results of the magnetic field by the magnet having a square magnet front and is a diagram showing the physical relationship between the magnet having the square magnet front and the cuvette.
Figure 10B:
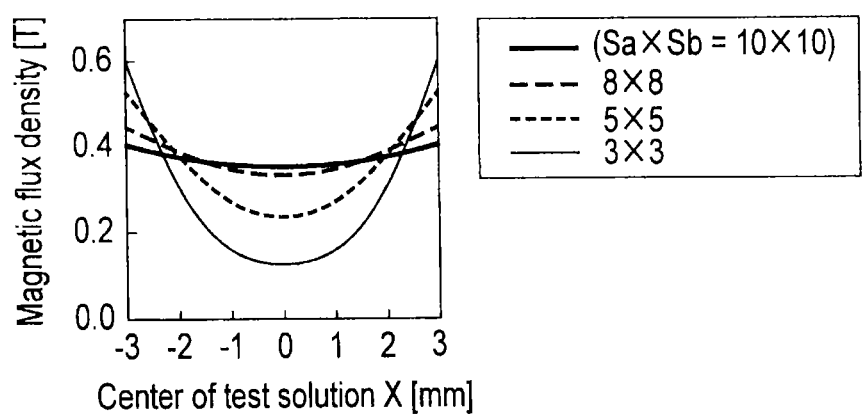
FIG. 10B is a diagram showing calculation results of the magnetic field by the magnet having the square magnet front and is a diagram showing the graph showing the spatial distribution in the X direction of the magnetic flux density by the magnet of FIG. 10A.

In the calculation of the magnetic field distribution, a square shape and a rectangular shape are adopted as the shape of the magnet front surface of the magnet. FIGS. 10A and 10B are diagrams showing calculation results of the magnetic field distribution by a magnet having a square magnet front surface. FIG. 10A shows the physical relationship between the magnet having a square magnet front surface and the cuvette and FIG. 10B is a graph showing the spatial distribution concerning the X direction of the magnetic flux density by the magnet in FIG. 10A. As shown in FIG. 10A, the length of the magnet front surface along the Z direction is set to Sa and the length of the magnet front surface along the Y direction is set to Sb. The graph in FIG. 10B shows magnetic flux densities in each case when the length Sa and the length Sb are 3, 5, 8, 10 mm. The magnetic flux densities in FIG. 10B show magnetic flux densities on an axis A2 passing through the center of a pair of rectangular neodymium magnets. As shown in FIG. 10B, the magnetic flux density significantly falls in the center of the cuvette 31 in the X direction with the decreasing lengths Sa, Sb and the magnetic flux density approaches uniformity with the increasing lengths Sa, Sb. As described above, the magnetic field distribution is more distorted with an increasing distance from the center of the magnet to the periphery. For a magnet which is 3 mms on a side, the test solution contact surface is larger than the magnet front surface. Thus, in the case of a magnet which is 3 mms on a side, the magnetic flux density falls significantly in an edge portion of the magnet or a region of the test solution facing the outside of the edge portion and so the concentration distribution of magnetic particles becomes extremely non-uniform. For a magnet which is 10 mms on a side, by contrast, the magnet front surface can be made larger than the test solution contact surface if the height of the test solution is made sufficiently lower than 10 mm. In this case, the magnetic flux density distribution is made flat not only on A2, but also in other regions and so the concentration distribution of magnetic particles can be made uniform over the entire test solution regardless of the elapsed time.

Figure 11A:
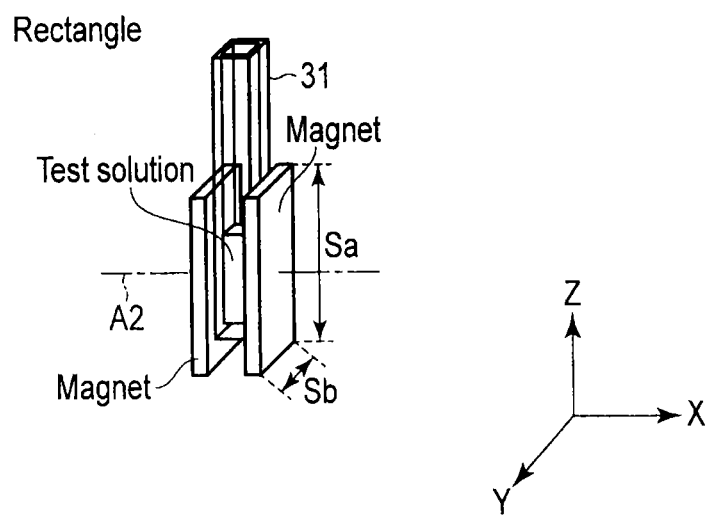
FIG. 11A is a diagram showing calculation results of the magnetic field by the magnet having a rectangular magnet front and is a diagram showing the physical relationship between the magnet having the rectangular magnet front and the cuvette.
Figure 11B:
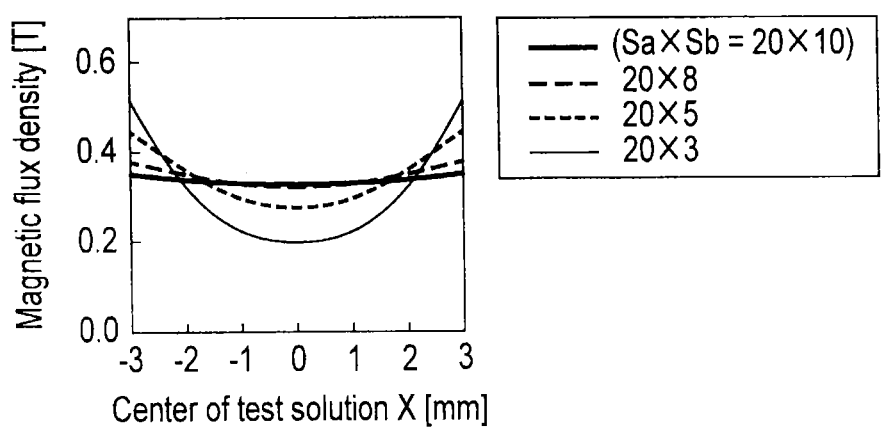
FIG. 11B is a diagram showing calculation results of the magnetic field by the magnet having the rectangular magnet front and is a diagram showing the graph showing the spatial distribution in the X direction of the magnetic flux density by the magnet of FIG. 11A.

FIGS. 11A and 11B are diagrams showing simulation results of the magnetic field distribution by a magnet having a rectangular magnet front surface. FIG. 11A shows the physical relationship between the magnet having a rectangular magnet front surface and the cuvette and FIG. 11B is a graph showing the spatial distribution of the magnetic flux density along the X direction by the magnet in FIG. 11A. FIGS. 11A and 11B shows each magnetic field distribution when the length Sa of the magnets in the Z direction is commonly set to 20 mm and the length Sb in the Y direction is 3, 5, 8, 10 mm. The magnetic flux densities in FIG. 11B show magnetic flux densities on the axis A2 passing through the center of a pair of rectangular neodymium magnets. The magnetic flux density on the axis A2 significantly falls in the center of the cuvette 31 with the decreasing length Sb and the magnetic flux density becomes substantially uniform with the increasing length Sb. When a magnet having a magnet front surface smaller than a test solution contact surface, like a magnet whose length Sb is 3 mm, is arranged, the concentration distribution of magnetic particles is significantly distorted. In contrast, when a magnet having a magnet front surface larger than a test solution contact surface, like a magnet whose length Sb is, for example, 10 mm, is arranged, the magnetic flux density becomes substantially uniform over the entire test solution. Accordingly, when a magnet having a magnet front surface larger than a test solution contact surface is arranged, the concentration distribution of magnetic particles can be made uniform over the entire test solution regardless of the elapsed time.

If, as described above, the concentration distribution of magnetic particles is non-uniform, measured results such as absorbance and turbidity of the test solution change in accordance with changes of the liquid volume of the test solution. The inventors optically measured absorbance by changing the geometrical arrangement of the magnet and the liquid volume of the test solution. The measurement of absorbance will be described in detail below.

In the measurement of absorbance, the inventors used dummy buffer solutions as a sample and a first reagent, and a solution obtained diluting magnetic particles Therma-Max® by Chisso Corporation (Magnabeat Incorporated) with a buffer solution as a second reagent. First, the sample and the first reagent are discharged into the cuvette 31 immersed in a constant temperature bath at 37° C. and stirred and next, the second reagent is discharged and stirred. The magnetic particles Therma-Max(R) have the particle size of about 100 nm in a storage state at low temperature, but aggregate with a rising temperature and are more likely to be sucked by a magnetic force. After magnetic particles are discharged into the cuvette 31, the inventors optically measured absorbance of the test solution and measured changes in concentration of magnetic particles.

In the measurement of absorbance, the size of the magnet and the installation position of the magnet with respect to the cuvette are considered as the geometrical arrangement of the magnet and 1×5×5 mm (square) and 1×5×10 mm (rectangular) are adopted as the sizes of the magnet. Rectangular neodymium magnets are used as the magnets. The inventors measured temporal changes of absorbance by changing the total liquid volume of the test solution in each geometrical arrangement. In the present measurement, the total liquid volume of the test solution is set to four stages shown in FIG. 12. FIG. 12 shows the fluid volume of the sample [µL], the fluid volume of the first reagent [µL], the fluid volume of the second reagent [µL], the fluid volume of intruding water [µL], and the height [mm] of the liquid for each total fluid volume [µL] of four stages of the test solution. As shown in FIG. 12, the total liquid volume of the test solution is set to 110 µL, 165 µL, 220 µL, and 275 µL. In each total liquid volume, the mixing ratio of magnetic particles in the test solution is maintained constant. The measuring wavelength is set to 416 nm. The photometry position is set to the height 2.5 mm above the inner bottom of the cuvette 31, that is, the bottom of the test solution. Dimensions of inner walls of the cuvette 31 are: X direction×Y direction=4×5 mm. The height (liquid height) of the test solution in each total liquid volume is as shown in FIG. 12.

Figure 13A:
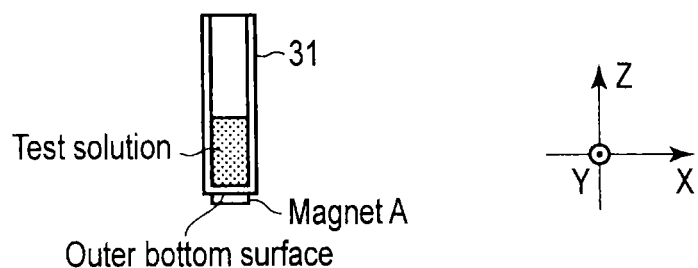
FIG. 13A is a diagram showing an arrangement example of a magnet A (X direction length×Y direction length×Z direction length=5×5×1 mm (polarized in the 1 mm direction)) on an outer bottom surface of the cuvette.
Figure 13B:
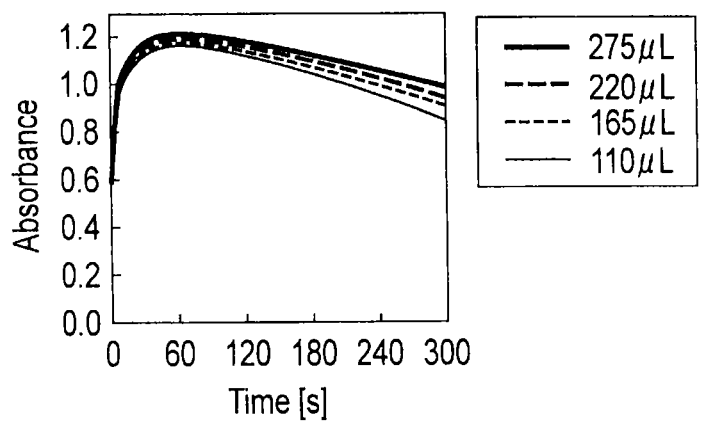
FIG. 13B is a diagram showing temporal change curves of absorbance for each total fluid volume of the test solution in FIG. 12 for the arrangement in FIG. 13A.
Figure 15A:
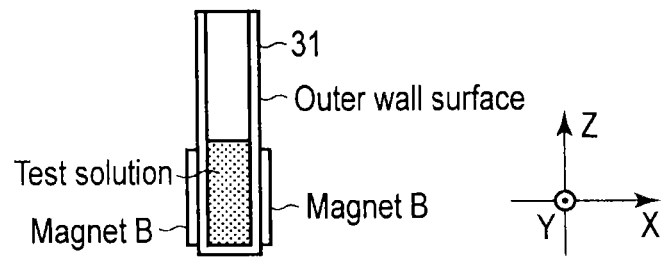
FIG. 15A is a diagram showing an arrangement example of a magnet B (X direction length×Y direction length×Z direction length=1×5×10 mm) on the outer wall surface opposite to the contact surface of the test solution of the cuvette.
Figure 15B:
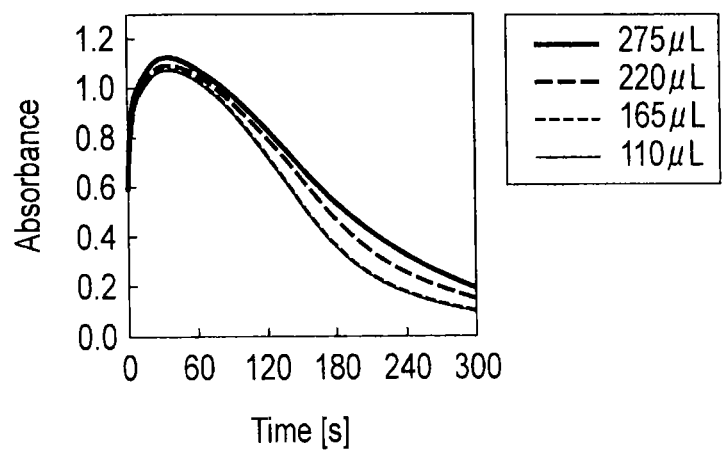
FIG. 15B is a diagram showing temporal change curves of absorbance for each total fluid volume of the test solution in FIG. 12 for the arrangement in FIG. 15A.

FIGS. 13A and 13B are diagrams showing temporal change curves of absorbance for each total liquid volume of the test solution in FIG. 12 when the magnet A (X direction length×Y direction length×Z direction length=5×5×1 mm) is arranged on an outer bottom surface of the cuvette 31. FIGS. 14A and 14B are diagrams showing temporal change curves of absorbance for each total liquid volume of the test solution in FIG. 12 when the magnets A are arranged on outer wall surfaces opposed to the test solution contact surface of the cuvette. FIGS. 15A and 15B are diagrams showing temporal change curves of absorbance for each total liquid volume of the test solution in FIG. 12 when the magnets B (X direction length×Y direction length×Z direction length=1×5×10 mm) are arranged on outer wall surfaces opposed to the test solution contact surface of the cuvette. In the absorbance measurements, the inventors prepared five combinations of the magnet and cuvette for each geometrical arrangement. In each of the five combinations, absorbance in four total liquid volumes was measured. Temporal change curves shown in FIGS. 13B, 14B, and 15B show averages of the five temporal change curves in the same geometrical arrangement. Variations of temporal change curves are sufficiently small among five curves in the same geometrical arrangement, which led to the discovery that there is no significant difference among five curves in the same geometrical arrangement. On the other hand, as shown in FIGS. 13B, 14B, and 15B, the inventors found that when the total liquid volumes are different, temporal change curves are significantly different. Temporal changes of absorbance in each geometrical arrangement will be described in detail below.

When, as shown in FIG. 13A, the magnet A is pasted to the outer bottom of the cuvette 31, the amount of decrease in absorbance over time is relatively small and the amount of decrease in absorbance over time decreases with an increasing liquid volume of the test solution. Because the magnet is pasted to the outer bottom of the cuvette 31, magnetic particles in the test solution are attracted downward to the magnet. When the magnet A is pasted to the outer bottom of the cuvette 31, the magnetic field rapidly attenuates with an increasing distance from the outer bottom of the test solution. Accordingly, with an increasing distance from the outer bottom of the cuvette 31, the magnetic flux density in the test solution attenuates and the traveling speed of magnetic particles slows down. Thus, when the magnet is pasted to the outer bottom of the cuvette 31, compared with a case when the magnet is pasted to the outer wall surface of the cuvette 31, it takes a long time for magnetic particles above the photometry position to reach the outer bottom of the cuvette 31 by passing the photometry position and the lowering speed of absorbance is slow. In addition, the number of magnetic particles moving downward from above the photometry position increases with an increasing total liquid volume of the test solution. In other words, the amount of decrease in absorbance over time decreases with an increasing total liquid volume.

When, as shown in FIG. 14A, the magnets A are pasted to the lower outer wall corresponding to the test solution contact surface of the cuvette 31, like in FIG. 13A, the amount of decrease in absorbance over time decreases with an increasing total liquid volume of the test solution. However, if the total liquid volume is 110 µL, compared with a case of 165 µL, the absorbance falls rapidly over time. The reason for the fall is as follows. When the total liquid volume is 110 µL, the height of the liquid level of the test solution is 5.5 mm, which is substantially equal to the height of the upper end of the magnet A. When the total liquid volume is 165 µL or more, by contrast, the height of the liquid level of the test solution is 8.3 mm, which is higher than the upper end of the magnet A. That is, when the total liquid volume is 110 µL, the number of magnetic particles present above the photometry position is very small, but when the total liquid volume is 165 µL or more, the number of magnetic particles present above the photometry position is large. When the total liquid volume is 165 µL or more, magnetic particles present above the magnet A move downward over time. Thus, when the total liquid volume is 165 µL or more, the concentration of magnetic particles in the photometry position is higher than when the total liquid volume is 100 µL. In other words, when the total liquid volume is 165 µL or more, the amount of decrease in absorbance over time decreases with an increasing total liquid volume when compared with a case in which the total liquid volume is 110 µL.

When, as shown in FIG. 15A, the magnets B are pasted to the test solution contact surface of the cuvette 31, the absorbance rapidly decreases over time regardless of the total liquid volume. The temporal change curves for the total liquid volume of 110 µL and the total liquid volume of 165 µL substantially match. When the total liquid volume is 110 µL, the height of the test solution is 5.5 mm and when the total liquid volume is 165 µL, the height of the test solution is 8.3 mm. That is, when the total liquid volume is 110 µL or 165 µL, the height of the test solution is lower than the height of the magnet B. Therefore, when the total liquid volume is 110 µL or 165 µL, magnetic particles cannot be present in a position higher than the magnet B and no magnetic particle moves toward the photometry position from above the photometry position and, as a result, the absorbance is substantially the same even if the total liquid volumes are different. That is, by making the height of the magnet B higher than the height of the test solution, magnetic particles are prevented from moving toward the photometry position from above the photometry position and variations of absorbance caused by changes of the total liquid volume can be reduced.

Based on the above preliminary measurement test results, the inventors produces the automatic analyzer 1 including the magnet 41 that applies a magnetic field whose magnetic flux density is uniform over the entire test solution in the cuvette 31. Hereinafter, a detailed structure of the automatic analyzer 1 according to the present embodiment will be described.

The automatic analyzer 1 according to the present embodiment includes a magnetic field applying module on which the magnet 41 having the above geometrical arrangement is mounted for each of the cuvettes 31.

Figure 16:
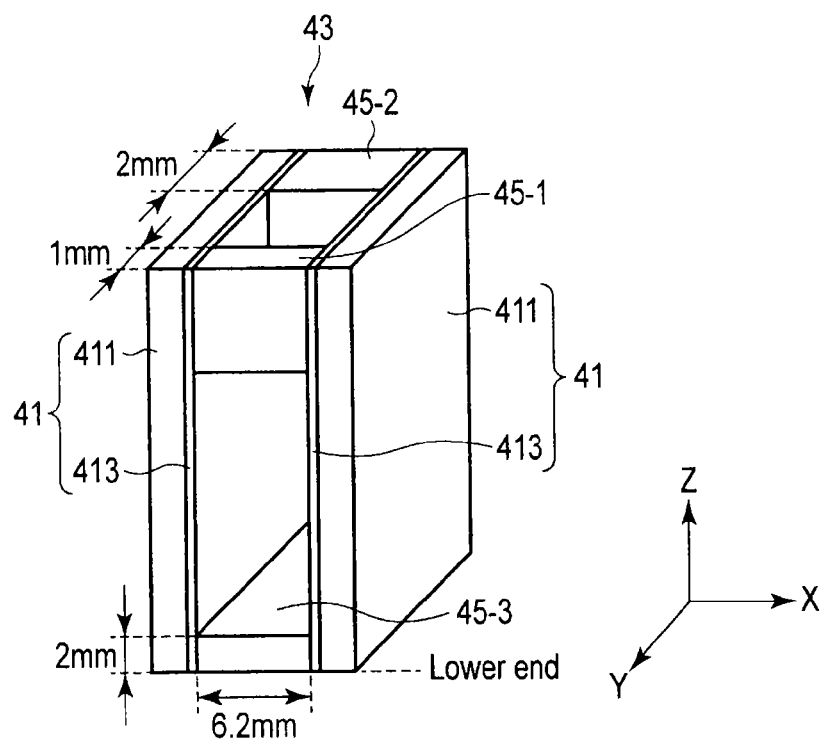
FIG. 16 is a perspective view of a magnetic field applying module according to the present embodiment.

FIG. 16 is a perspective view of a magnetic field applying module 43. As shown in FIG. 16, the magnetic field applying module 43 includes the magnet 41 and a spacer 45. The two magnets 41 are arranged by opposing S and N poles across a cuvette along the X direction. The magnet 41 is formed from a permanent magnet 411 and a soft magnetic plate 413. For example, as the permanent magnet 411, a neodymium magnet or the like, as described above, is used. The soft magnetic plate 413 is provided between the permanent magnet 411 and the cuvette 31. Typically, the soft magnetic plate 413 is pasted to a surface of the permanent magnet 411 on the cuvette 31 side. The soft magnetic plate 413 is formed by molding a soft magnetic material into a plate shape. As the soft magnetic material, a metal such as iron, nickel, and cobalt, an alloy such as permalloy and supermalloy, or magnetic stainless may be used. In the above description, the magnet 41 is assumed to be formed from the permanent magnet 411 and the soft magnetic plate 413. However, the present embodiment is not limited to such an example. For example, the magnet 41 may use, instead of the permanent magnet 411, an electromagnet.

The soft magnetic plate 413 is provided to improve the degree of uniformity of a magnetic field generated by the permanent magnet 411. Hereinafter, the mechanism to improve the degree of uniformity of a magnetic field by the soft magnetic plate 413 will be described. The permanent magnet 411, particularly the permanent magnet 411 containing a rare earth element can generate a strong magnetic field strength. However, the magnetic field distribution may be distorted by variations of material or variations of polarization. Resulting from a distortion of the magnetic field distribution, the concentration distribution of magnetic particles becomes non-uniform, leading to variations of measured values from the cuvette 31 to the cuvette 31. The soft magnetic plate 413 is formed from a soft magnetic material having high permeability. By arranging the soft magnetic plate 413 between the permanent magnet 411 and the cuvette 31 such that a magnetic flux generated by the permanent magnet 411 passes through the soft magnetic plate 413, uniformity of the magnetic flux density on the front side of the magnet 41 can be improved. As a result, the distortion in the magnetic field distribution in the test solution can be reduced so that non-uniformity in the concentration distribution of magnetic particles and variations of measurement results from the cuvette 31 to the cuvette 31 can be reduced. To enhance uniformity of the magnetic flux density on the front side of the permanent magnet 411, surfaces of the soft magnetic plate 413 and the permanent magnet 411 opposed to each other may have substantially the same area. Incidentally, the soft magnetic plate 413 may be provided on a surface of the permanent magnet 411 on the opposite side of the cuvette 31 or on both surfaces of the permanent magnet 411. In the present embodiment, for example, the material of the permanent magnet 411 may be N48M (manufactured by Shin-Etsu Chemical) with dimensions of X direction length×Y direction length×Z direction length=1.5×10×22 mm (magnetized in the X direction) and the soft magnetic plate 413 may have dimensions of X direction length×Y direction length×Z direction length=0.3×10×22 mm. The magnet 41 is formed by pasting the soft magnetic plate 413 to the surface of the permanent magnet 411 opposed to the cuvette 31.

The two magnets 41 are connected via the spacer 45 so as to have the above geometrical arrangement. To be concrete, the interval between the magnets 41 along the X direction is set to 6.2 mm. That is, the width of the spacer 45 along the X direction is substantially 6.2 mm, which is substantially the same interval as that between the magnets 41 along the X direction. The spacer 45 includes, for example, a first spacer 45-1, a second spacer 45-2, and a third spacer 45-3. To fix the two magnets 41 to a predetermined interval, the two magnets 41 are connected via the first spacer 45-1, the second spacer 45-2, and the third spacer 45-3. The first spacer 45-1 and the second spacer 45-2 are connected in an upper portion of the two magnets 41 to form a space allowing the cuvette 31 to be inserted into the magnetic field applying module 43. The third spacer 45-3 on which the cuvette 31 can be placed is connected in a lower portion of the two magnets 41. A cuvette is accommodated in a space surrounded by the magnets 41 and each of the spacers 45. The two magnets 41 are connected via the third spacer 45-3 such that the lower end of each of the magnets 41 protrudes downward from the top surface of the third spacer 45-3 by 2 mm. If this structure is adopted, the lower end of the magnet 41 protrudes downward from the outer bottom of a cuvette 100 by 2 mm when the cuvette 31 is inserted into the magnetic field applying module 43. In addition, the two magnets are connected via spacers such that regarding the forward direction and the backward direction of the Y direction, the magnet protrudes to the outer side from the cuvette by 1 mm and 2 mm respectively. The magnetic field applying module 43 is arranged circumferentially when mounted on a bow plate 47 and so the magnetic field tends to decrease more outside the circumference than inside the circumference. Thus, the length of the spacer in the Y direction is set to 1 mm for 45-1 and 2 mm for 45-2 and the magnetic field applying module 43 is mounted on the bow plate such that the spacer 45-2 is on the outer circumferential side. Accordingly, the decrease of a magnetic field outside the circumference can be inhibited so that uniformity of the magnetic field in the Y direction can be enhanced. The thickness of bottom plate of the cuvette is 1 mm and thus, the magnet front surface can be made larger than the test solution contact surface by limiting the height from the inner bottom of the cuvette 31 to the liquid level of the test solution to substantially 19 mm.

Figure 17:
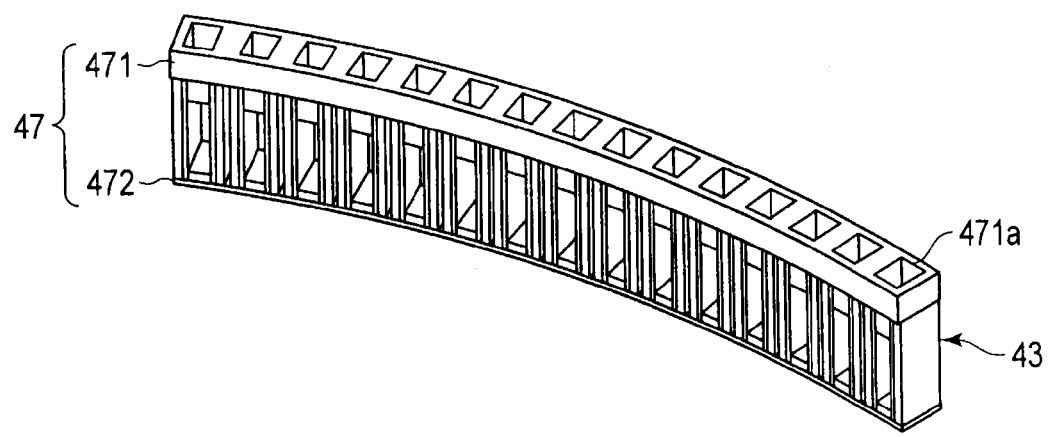
FIG. 17 is a perspective view of a bow plate according to the present embodiment.

The reaction disk 11 has a plurality of the bow plates 47 arranged circumferentially mounted thereon. FIG. 17 is a perspective view of the bow plate 47. As shown in FIG. 17, each of the bow plates 47 has a bow shape and is a support removably holding a plurality of magnetic field applying modules 43. The bow plate 47 and the reaction disk 11 are set to have substantially the same curvature so that the bow plate 47 can be accommodated in the reaction disk 11. The magnetic field applying modules 43 is equidistantly arranged in each of the bow plates 47. For example, each of the bow plates 47 has a structure capable of holding 15 units of the magnetic field applying module 43. Each of the magnetic field applying modules 43 is arranged with the magnets 41 opposite to each other so that light from the light source 210 can pass between the magnets 41.

To be concrete, each of the bow plates 47 is formed of a first plate 471 and a second plate 472. The first plate 471 is a support that supports an upper portion of the cuvette 31 and the second plate 472 is a support that supports a lower portion of the cuvette 31. The first plate 471 has an opening 471a through which the cuvette 31 is put into or removed from the magnetic field applying module 43 formed therein. The arrangement pitch of the opening 471a and the arrangement pitch of the magnetic field applying modules 43 are set substantially the same. The first plate 471 and the second plate 472 are fixed in a state in which the cuvettes 31 are sandwiched from above and from below. The bow plate 47 is accommodated in the reaction disk 11 in a state in which the magnetic field applying modules 43 are mounted on the bow plate 47. Accordingly, the magnetic field applying modules 43 can be fixed inside the reaction disk 11. With the magnetic field applying modules 43 fixed inside the reaction disk 11, variations of measured values accompanying positional shifts of the magnetic field applying modules 43 can be reduced.

In the above description, it is assumed that the magnetic field applying modules 43 are mounted on the bow plate 47. However, the present embodiment is not limited to such an example. If the magnetic field applying module 43 can directly be fixed to the reaction disk 11, the magnetic field applying module 43 may directly be arranged inside the reaction disk 11 without being mounted on the bow plate 47.

The inventors optically measured absorbance of each of the 15 cuvettes 31 held by the bow plate 47. Measurements of absorbance were made for the four total liquid volumes of the test solution in FIG. 12. Measurements of absorbance were made three times for each of the cuvettes 31. Measured values of the two cuvettes held on both ends of the bow plate 47 were different from measured values of other remaining 13 cuvettes. For the 13 cuvettes which remain after excluding two cuvettes on both ends of the bow plate 47, variations of measured values for each measurement and variations among the cuvettes 31 are within a permissible range.

Figure 18:
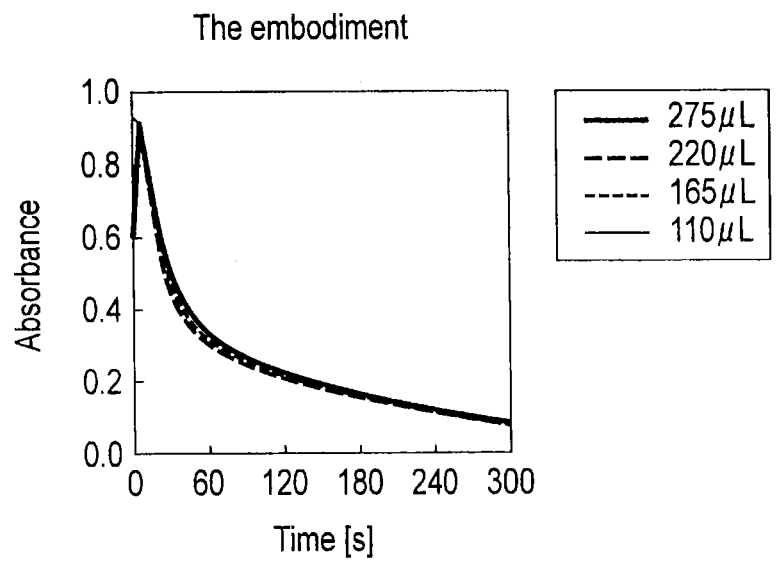
FIG. 18 is a diagram showing temporal change curves of absorbance for each total fluid volume of the test solution in FIG. 12 when the magnet having a geometrical arrangement according to the present embodiment is used.

FIG. 18 is a diagram showing temporal change curves of absorbance for each total fluid volume of the test solution in FIG. 12 when the magnet 41 having a geometrical arrangement according to the present embodiment is used.

The temporal change curves in FIG. 18 are averages of measured values of the remaining 13 cuvettes excluding two containers on both ends of the bow plate 47. When, as shown in FIG. 18, the magnets 41 having a geometrical arrangement according to the present embodiment is used, temporal change curves of absorbance substantially match regardless of differences of total liquid volumes.

In FIG. 18, compared with cases of FIGS. 13, 14, and 15, variations of absorbance accompanying of changes of the liquid volume of the test solution are reduced. That is, when the magnet front surface 41f is relatively larger than the test solution contact surface 31c, the concentration distribution of magnetic particles in the test solution can be made uniform and variations of absorbance resulting from differences of liquid volumes of the test solution can be reduced when compared with a case in which the magnet front surface 41f is relatively smaller than the test solution contact surface 31c.

As described above, the magnetic flux density in the photometry position changes depending on the relative physical relationship of magnets. The inventors found the geometrical arrangement of the magnets 41 that can reduce changes of the magnetic flux density in accordance with the change of photometry position. Hereinafter, the geometrical arrangement will be described in detail.

Figure 19:
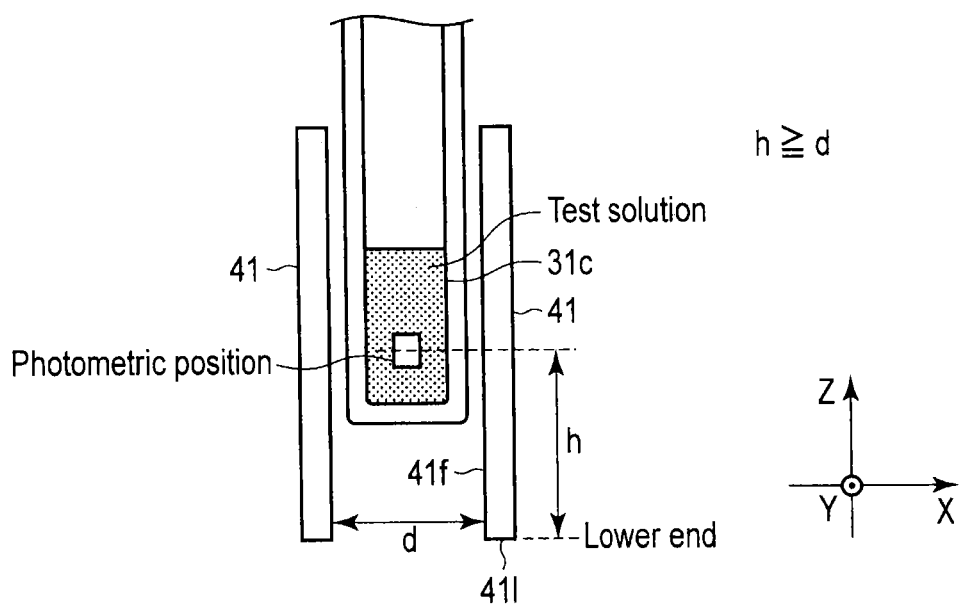
FIG. 19 is a diagram showing the physical relationship between the magnet and the cuvette according to the present embodiment.

FIG. 19 is a diagram showing the physical relationship between the magnet 41 and the photometry position. As shown in FIG. 19, the photometry position is set to a height such that light passes through the test solution in the cuvette 31. The two magnets 41 are arranged on both sides concerning the X direction of the cuvette 31. The two magnets 41 are arranged with a distance interval d therebetween. The difference of height between the center concerning the Z direction of the photometry position and the lower end of the magnet 41 is set to h. The magnet 41 has the magnet front surface 41f larger than the test solution contact surface 31c to make the magnetic flux density spatially substantially uniform. Typically, the magnet front surface 41f has a rectangular shape long in the Z direction. Further, the magnet 41 may have a geometrical arrangement satisfying $d \leq h$ to reduce the magnetic flux density in the photometry position. The reason therefor is as follows.

When the two magnets 41 long in the Z direction are arranged opposite to each other, regarding the magnetic field distribution formed in a region between the two magnets 41, the magnetic flux density near the center portion concerning the Z direction of the magnet 41 becomes substantially flat concerning the Z direction with an increasing length Sa concerning the Z direction of the magnet with respect to a distance d between the magnets. The lines of magnetic force near both ends concerning the Z direction of the magnet 41 dissipate to the outer side of the magnet 41 and so the magnetic flux density decreases. Therefore, when the cuvette 31 is installed between the magnets 41, it is necessary to install the outer bottom of the cuvette 31 to a position higher than the lower end of the magnet to secure uniformity of the concentration distribution of magnetic particles without being affected by the decrease of the magnetic flux density near the lower end of the magnet 41. Physically, the magnetic flux density decreases in a region up to the distance d from the lower end of the magnet. That is, if the magnets 41 and the cuvette 31 are installed such that the height h becomes equal to the distance d or more, a gradient of the magnetic flux density hardly arises along the up and down direction (Z direction) near the photometry position in the test solution. By setting the geometrical arrangement of the magnets as described above, the concentration distribution of magnetic particles near the photometry position in the test solution can be prevented from becoming non-uniform.

The photometry position may different in accordance with settings of the automatic analyzer 1. Therefore, when the magnets 41 are installed, if the difference of height between structurally the lowest photometry position where light measurement can be made (hereinafter, called the lowest photometry position) and the lower end of the magnet 41 is h, the magnets 41 may be installed such that the relationship of $d \leq h$ is satisfied. In this case, even if the photometry position is changed to a position higher than the lowest photometry position, the relationship of $d \leq h$ is maintained and therefore, the influence of the change of the photometry position on measurement results can be reduced to a minimum.

The inventors measured absorbance when the relationship of $d \leq h$ is satisfied and the relationship is not satisfied. Hereinafter, the measurements results will be described.

Figure 20A:
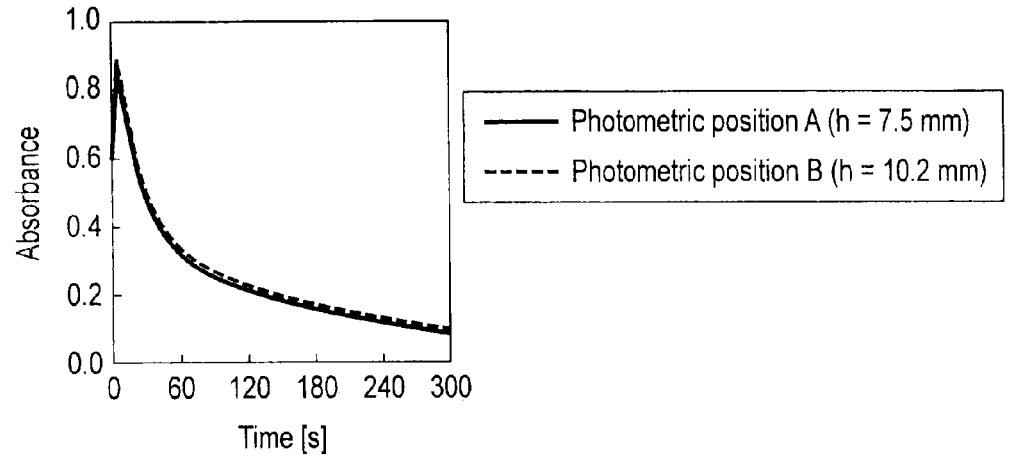
FIG. 20A is a diagram showing the graph showing temporal change curves of absorbance in a photometry position A and a photometry position B when the magnet having the geometrical arrangement according to the present embodiment is used.
Figure 20B:
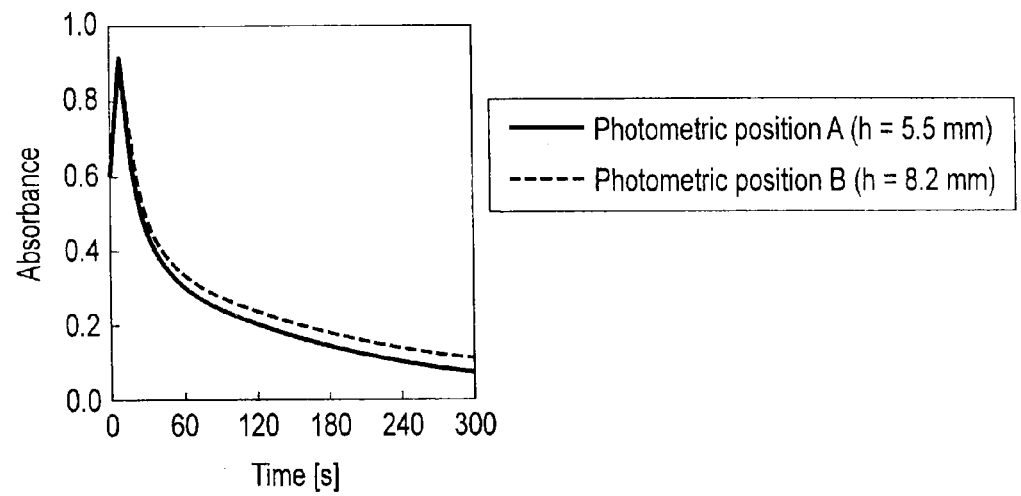
FIG. 20B is a diagram showing the graph showing temporal change curves of absorbance in the photometry position A and the photometry position B when the magnet having the geometrical arrangement according to a comparative example is used.

FIGS. 20A and 20B are diagrams individually showing the graphs showing temporal change curves of absorbance in a photometry position A and a photometry position B when the magnet having the geometrical arrangement according to the present embodiment and the magnet having the geometrical arrangement according to a comparative example are used. FIG. 20A shows temporal change curves of absorbance in the photometry position A and the photometry position B when the magnet having the geometrical arrangement according to the present embodiment is used and FIG. 20B shows temporal change curves of absorbance in the photometry position A and the photometry position B when the magnet having the geometrical arrangement according to the comparative example is used. In FIGS. 20A and 20B, the total liquid volume of the test solution is set to 220 μL and the liquid volume of each solution in the test solution is set according to FIG. 12. Temporal change curves in FIGS. 20A and 20B are averages of the 13 cuvettes 31 among the 15 cuvettes 31 in the bow plate 47 excluding cuvettes on both ends. Variations of measured values among the cuvettes 31 are within a permissible range.

First, the geometrical arrangement according to the comparative example in FIG. 20B will be described. A neodymium magnet manufactured by Shin-Etsu Chemical is used as a permanent magnet of the magnet. The neodymium magnet uses N48M as its material, has the dimensions of 22×10×1.5 mm, has the magnetization direction of the X direction (thickness direction of the neodymium magnet), and is plated with Ni. As the soft magnetic plate, the material SUS430 with the dimensions 22×10×0.3 mm is used. The thickness of the sidewall of the cuvette 31 is 1.0 mm. The distance d between the magnets is set to 6.2 mm. The magnets are arranged so that the lower end of the magnets is positioned 2 mm below the outer bottom of the cuvette 31. The photometry position A is set 2.5 mm above the lower end of the test solution contact surface of the cuvette 31. For the photometry position A, the height h is 5.5 mm. For comparison with the photometry position A, the photometry position B is set 2.7 mm above the photometry position A. That is, for the photometry position B, the height h is 8.2 mm. Therefore, in FIG. 20B, the photometry position A satisfies $d > h$ and the photometry position B satisfies $d \leq h$.

In the geometrical arrangement according to the comparative example, as shown in FIG. 20B, temporal change curves are slightly shifted between the photometry position A and the photometry position B. The amount of decrease in absorbance over time is larger in temporal change curves concerning the photometry position A than in temporal change curves concerning the photometry position B. The standard deviation of variations of absorbance among the cuvettes 31 in the same photometry position when the measurement is completed is about 0.0035 and the difference of the average absorbance in different photometry positions is 0.0315. That is, the difference of the average absorbance in different photometry positions is greater than variations among the cuvettes 31 by an order of magnitude or so, which is considered to be a significant difference. From the above results, the inventors found that measurements results from the geometrical arrangement according to the comparative example are affected by differences of photometry positions.

Next, the geometrical arrangement according to the present embodiment in FIG. 20A will be described. A neodymium magnet (material: N48M) manufactured by Shin-Etsu Chemical is used as the permanent magnet 411. The permanent magnet has the dimensions of 24×10×1.5 mm, has the magnetization direction of the X direction (thickness direction of the neodymium magnet), and is plated with Ni. As the soft magnetic plate 413, the material SUS430 with the dimensions 24×10×0.3 mm is used. Like the conventional example, the thickness of the sidewall of the cuvette 31 is set to 1.0 mm and the distance d between the magnets 41 is set to 6.2 mm. In the geometrical arrangement according to the present embodiment, the magnets 41 are arranged such that the lower end of the magnet 41 is positioned 4 mm below the outer bottom of the cuvette 31. The photometry position A is set 2.5 mm above the lower end of the test solution contact surface of the cuvette 31. For the photometry position A, the height h is 7.5 mm. The photometry position B is set 2.7 mm above the photometry position A. That is, for the photometry position B, the height h is 10.2 mm. Therefore, in FIG. 20A, both of the photometry position A and the photometry position B satisfy d≤h.

In the geometrical arrangement according to the present embodiment, as shown in FIG. 20A, temporal change curves of absorbance related to the photometry position A and temporal change curves of absorbance related to the photometry position B substantially match. Variations of absorbance among cuvettes in the same photometry position is approximately the same as the difference of the average absorbance in different photometry positions. That is, in the case of the geometrical arrangement according to the present embodiment, there is no significant difference among temporal change curves in different photometry positions. From the above measurement results, it is verified that variations of measurement results caused by changing the photometry position can be prevented by using magnets having the geometrical arrangement that satisfies d≤h. Therefore, by using the magnets 41 having the geometrical arrangement that satisfies d≤h, stable measurement results can be obtained independent of the apparatus configuration.

In the geometrical arrangement according to the comparative example, the difference of temporal change curves between the photometry position A and the photometry position B is considered to be caused by different magnetic field environments between the photometry position A and the photometry position B. The inventors calculated the distribution along the Z direction of the magnetic flux density concerning the X direction based on the magnetic field analysis.

FIG. 21 is a diagram showing position change curves along the Z direction of the magnetic flux density concerning the X direction in the geometrical arrangement according to the comparative example (the lower end of the magnet protrudes 2 mm below the outer bottom of the cuvette) and the geometrical arrangement according to the present embodiment (the lower end of the magnet protrudes 4 mm below the outer bottom of the cuvette). In FIG. 21, the coordinate of the Z axis is set such that Z=0 corresponds to the inner bottom of the cuvette 31, that is, the lower end of the test solution and Z takes a positive value on the upper side of the test solution. The photometry position A corresponds to Z=2.5 and the photometry position B corresponds to Z=5.2. In the comparative example, as shown in FIG. 21, the decrease of the magnetic flux density starts in a region near the bottom of the test solution toward the −Z direction. Thus, the gradient of the magnetic flux density in a region near the bottom inside the test solution becomes larger than the gradient of the magnetic flux density in a region in the +Z direction therefrom. Therefore, for the photometry position A, compared with the photometry position B, magnetic particles are attracted to the magnet more quickly and, as a result, the amount of decrease in absorbance in accordance with the elapsed time increases. To reduce such variations of temporal changes in absorbance in accordance with the photometry position, it is necessary to inhibit the decrease of the magnetic flux density near the lower end of the test solution and to increase a region in which the magnetic flux density is flat along the Z direction. For this purpose, the geometrical arrangement satisfying d≤h may be set. In the geometrical arrangement according to the present embodiment, as shown in FIG. 21, the region in which the magnetic field distribution is flat extends up to Z=0 and flatness of the magnetic field distribution near the lower end of the test solution is clearly improved.

When the magnet 41 and the cuvette 31 are alternately arranged along the circumference, as shown in FIG. 2, a pair of the magnets 41 across the cuvette 31 may not be arranged in parallel. In such a case, as shown in FIG. 22, the distance d between magnets is different depending on the position in the Y direction. In this case, the maximum distance between magnets of distances between magnets in a plurality of positions in the Y direction passing through the test solution may be set as the distance d. For example, a straight line Lx touching a surface 31x parallel to the X direction of inside surfaces of the cuvette 31 is considered. The distance between intersections P1, P2 f the straight line Lx and the magnet front surface 41f of each of the magnets 41 may be set as the distance d. In addition, as described above, the height h may be set as the distance between the lowest photometry position and the lower end of the magnet 41. With the magnets 41 provided in the geometrical arrangement in which the distance d and the height h set as described above satisfy d≤h, variations of measured values resulting from the difference of the photometry positions can be inhibited.

The automatic analyzer 1 according to the present embodiment includes the reaction disk 11, the magnets 41, and the photometric mechanism 27. The reaction disk 11 accommodates the cuvette 31 for the test solution containing a sample and magnetic particles. The magnet 41 applies a magnetic field to the test solution in the cuvette 31. The photometric mechanism 27 includes the light source 210 and the detector 220. The light source 210 irradiates light toward the test solution in the cuvette 31. The detector 220 is provided in a position opposed to the light source 210 across the cuvette 31 to detect light from the test solution. The magnets 41 have a geometrical arrangement such that the magnetic flux density of the magnetic field in the test solution inside the cuvette 31 is substantially uniform. To be concrete, a magnet having the magnet front surface 41f larger than the test solution contact surface 31c of the cuvette 31 is used as the magnet 41. In addition, the magnets 41 are arranged such that the difference h of height between the photometry position and the lower end of the magnet 41 becomes larger than the distance d between magnets.

If the above configuration is adopted, magnetic particles can be separated from the test solution by a magnetic force caused by the magnet 41 while the concentration distribution of magnetic particles in the test solution is maintained uniform. As a result, variations of measured values caused by changes of the liquid volume of the test solution or the photometry position can be reduced and the influence on measurement results can be inhibited. Therefore, the automatic analyzer 1 according to the present embodiment can obtain high-precision inspection results. In addition, the development cost of the automatic analyzer 1 can be reduced. Even if the relative physical relationship of the test solution and the magnet 41 varies among the different cuvettes 31 due to producing tolerances of the size of the cuvette 31 or the fixing position, variations of inspection results among the different cuvettes 31 can be reduced.

Next, application examples of an automatic analyzer according to the present embodiment will be described.

APPLICATION EXAMPLE 1

The automatic analyzer 1 according to the above embodiment is configured such that a magnetic field from the magnet 41 is always applied to the cuvette 31. In this case, magnetic particles are attracted to the inner wall of the cuvette 31 by the magnet 41 immediately after magnetic particles being discharged into the cuvette 31. Thus, the efficiency of reaction between magnetic particles and trace molecules to be measured may not be sufficient. Also when the cuvette 31 is cleaned by the cleaning mechanism 29, magnetic particles are attracted to the inner wall of the cuvette 31 by the magnet 41 and so it is difficult to wash out magnetic particles from the cuvette 31.

The automatic analyzer 1 according to the application example 1 has a configuration capable of switching application and non-application of a magnetic field to the cuvette 31. FIG. 23 is a schematic plan view of a periphery of the reaction disk 11 of the automatic analyzer 1 according to the application example 1. As shown in FIG. 23, the automatic analyzer 1 according to the application example 1 has a attaching and detaching mechanism 51 mounted outside the reaction disk 11 on a stage. In FIG. 23, other mechanisms such as the stirring mechanism 23 and the cleaning mechanism 29 are omitted.

The attaching and detaching mechanism 51 has a configuration capable of attaching and detaching the cuvette 31 arranged in an attaching/detaching position Pa on the reaction disk 11 with respect to the reaction disk 11. The mechanism 51 contains a driver that operates the mechanism 51 according to the control from the analysis mechanism controller 3. To be concrete, the mechanism 51 detaches the cuvette 31 from the reaction disk 11 to retract cuvette 31 from a magnetic field or attaches the cuvette 31 on the reaction disk 11 to apply a magnetic field to the cuvette 31 according to the control from the analysis mechanism controller 3. More specifically, the mechanism 51 moves the cuvette 31 arranged in the attaching/detaching position Pa to a retract position Pb outside the reaction disk 11 according to the control from the analysis mechanism controller 3. The attaching and detaching mechanism 51 also moves the cuvette 31 arranged in the retract position Pb to the attaching/detaching position Pa according to the control from the analysis mechanism controller 3. The means for moving the cuvette 31 by the attaching and detaching mechanism 51 may be any means capable of moving the cuvette 31. The attaching and detaching mechanism 51 may be able to attach/detach the cuvette 31 or, as shown in FIG. 23, the cuvettes 31. When the attaching and detaching mechanism 51 can attach/detach cuvettes 31, the removal mechanism may move the cuvettes together or individually.

However, targets to be removed by the attaching and detaching mechanism 51 are not limited to the cuvette 31. For example, the attaching and detaching mechanism 51 may attach or detach, instead of the cuvette 31, the magnet 41. In this case, a pair of the magnets 41 across the cuvette 31 to which no magnetic field should be applied are attached and detached by the mechanism 51. Alternatively, the cuvette 31 and the magnets 41 may be attached and detached together.

When the magnet 41 is moved from the attaching/detaching position Pa on the reaction disk 11, the magnetic flux density of a magnetic field applied to the unintended cuvettes 31 arranged around the moved magnet 41 may fluctuate. As a result, the concentration distribution of magnetic particles in the unintended cuvettes 31 may become non-uniform, adversely affecting measurement results. Therefore, the target to be attached and detached by the mechanism 51 is desirably the cuvette 31 rather than the magnet 41.

In the above description, the automatic analyzer 1 is mounted with the mechanism 51 capable of mechanically moving the cuvette 31 or the magnet 41 to switch application and non-application of a magnetic field to the cuvette 31. However, the means for switching application and non-application of a magnetic field according to the present embodiment is not limited to the above example. If, for example, the magnet 41 is formed from an electromagnet, an automatic analyzer 1 may be mounted with a current control apparatus as a means for switching application and non-application of a magnetic field. The current control apparatus controls the current supply to the electromagnet according to the control from the analysis mechanism controller 3. For example, the current control apparatus stops the current supply to a pair of electromagnets sandwiching the intended cuvette 31 therebetween to stop application of a magnetic field to the intended cuvette 31. On the other hand, the current control apparatus starts the current supply to the pair of electromagnets sandwiching the intended cuvette 31 therebetween to start application of a magnetic field to the intended cuvette 31.

As described above, the automatic analyzer 1 according to the application example 1 is mounted with a means for switching application and non-application of a magnetic field to the intended cuvette 31. Accordingly, after magnetic particles are discharged into the cuvette 31, a reaction of magnetic particles with trace molecules to be measured can be promoted by stopping application of a magnetic field to the cuvette 31. Also, the cuvette can be cleaned with high precision by stopping application of a magnetic field to the cuvette 31 to be cleaned.

APPLICATION EXAMPLE 2

FIG. 24 is a schematic plan view of the periphery of the reaction disk 11 of the automatic analyzer 1 according to the application example 2. As shown in FIG. 24, the automatic analyzer 1 according to the application example 2 is mounted with a demounting mechanism 53, a mounting mechanism 55, and a transport mechanism 57 outside the reaction disk 11.

The demounting mechanism 53 has a configuration capable of demounting the cuvette 31 arranged in a demounting position Pc on the reaction disk 11 from the reaction disk 11. The demounting mechanism 53 contains a drive apparatus that operates the demounting mechanism 53 according to the control from the analysis mechanism controller 3. To be concrete, the demounting mechanism 53 demounts the cuvette 31 from the demounting position Pc to retract the cuvette 31 from a magnetic field to arrange the cuvette 31 in a retract position Pd arranged in a position where the influence of a magnetic field from the magnet 41 can be ignored according to the control from the analysis mechanism controller 3. The retract position Pd is provided on the transport mechanism 57.

The mounting mechanism 55 has a configuration capable of mounting the cuvette 31 arranged in a waiting position Pe on the transport mechanism 57 on a mounting position Pf on the reaction disk 11. The mounting mechanism 55 contains a drive apparatus that operates the mounting mechanism 55 according to the control from the analysis mechanism controller 3. To be concrete, the mounting mechanism 55 arranges the cuvette 31 arranged in the waiting position Pe in the mounting position Pf to apply a magnetic field to the cuvette 31 according to the control from the analysis mechanism controller 3. The waiting position Pe is arranged in a position where the influence of a magnetic field from the magnet 41 can be ignored.

The transport mechanism 57 is installed in a position outside the reaction disk 11 on a stage and where the influence of a magnetic field from the magnet 41 can be ignored. The transport mechanism 57 has a configuration capable of transporting the cuvette 31 arranged in the retract position Pd to the waiting position Pe. The transport mechanism 57 contains a drive apparatus that operates the transport mechanism 57 according to the control from the analysis mechanism controller 3. To be concrete, the transport mechanism 57 repeats the movement and the stop at fixed time intervals according to the control from the analysis mechanism controller 3 to intermittently transport the cuvette 31 from the retract position Pd to the waiting position Pe. The transport mechanism 57 is realized by, for example, a belt conveyor. A cleaning position Pg and a stirring position Ph are provided in this order from the side of the retract position Pd between the retract position Pd and the waiting position Pe on the transport mechanism 57.

The cleaning mechanism 29 cleans the cuvette 31 arranged in the cleaning position Pg on the transport mechanism 57 using a cleaning fluid according to the control from the analysis mechanism controller 3. The stirring mechanism 23 stirs a sample and magnetic particles inside the cuvette 31 arranged in the stirring position Ph on the transport mechanism 57 using the stirrer 25 according to the control from the analysis mechanism controller 3.

Next, an operation example according to the analysis mechanism controller 3 according to the application example 2 will be described. The analysis mechanism controller 3 starts a process according to the application example 2 when the start of a determination process of trace molecules to be measured is instructed via the operation unit 6. First, while the cuvette 31 is retracted from a magnetic field by the magnet 41, a sample containing trace molecules to be measured and a reagent containing magnetic particles are discharged into the cuvette 31. The sample and magnetic particles are discharged, for example, on the transport mechanism 57. The cuvette 31 into which the sample and magnetic particles have been discharged is transported to the stirring position Ph by the transport mechanism 57 by repeating the movement and the stop. When the cuvette 31 is arranged in the stirring position Ph, the sample and magnetic particles in the cuvette are stirred by the stirring mechanism 23 using the stirrer 25. The cuvette 31 after stirring is transported to the waiting position Pe by the transport mechanism 57. When arranged in the waiting position Pe, the cuvette 31 is mounted in the mounting position Pf on the reaction disk 11 by the mounting mechanism 55. The cuvette 31 has a magnetic field applied from the magnet 41 by being mounted on the reaction disk 11. As described above, the magnets 41 have a geometrical arrangement such that the magnetic flux density becomes substantially uniform. Therefore, the concentration distribution of magnetic particles in the test solution inside the cuvette 31 changes while spatially remaining substantially uniform. The cuvette 31 mounted in the mounting position Pf crosses the photometry position on the reaction disk 11 a predetermined number of times while repeating the rotation and the stop by the reaction disk 11. The test solution in the cuvette 31 is optically measured by the photometric mechanism 27 each time the cuvette 31 crosses the photometry position. After optical measurements are made the predetermined number of times, the cuvette 31 is arranged in the demounting position Pc on the reaction disk 11 while repeating the rotation and the stop by the reaction disk 11. The cuvette 31 arranged in the demounting position Pc is moved from the reaction disk 11 to the retract position Pd on the transport mechanism 57 by the demounting mechanism 53. The cuvette 31 is retracted from a magnetic field by the magnet 41 by being demounted from the reaction disk 11. The cuvette 31 arranged in the retract position Pd is transported to the cleaning position Pg by the transport mechanism 57 by repeating the movement and the stop. The cuvette 31 arranged in the cleaning position Pg is cleaned by the cleaning mechanism 29 using a cleaning fluid.

This completes a determination process of the cuvette 31 by the analysis mechanism controller 3. The analysis mechanism controller 3 repeatedly performs the above process for each cuvette in parallel. Accordingly, the determination process of trace molecules to be measured can be performed for the cuvettes 31 in parallel.

As described above, magnetic particles are discharged into the cuvette 31 and stirred while detached from a magnetic field. Therefore, the efficiency of reaction of trace molecules contained in a sample and magnetic particles is improved so that sensitivity of detection of trace molecules can be enhanced. By making optical measurements in a magnetic field by the magnet 41 having the above geometrical arrangement, temporal changes of measured values such as absorbance and turbidity can be measured while uniformity of the concentration distribution of magnetic particles is maintained so that measured results with less variations can be obtained regardless of the liquid volume and the photometry position. By cleaning the cuvette 31 while detached from a magnetic field, the efficiency of washing out magnetic particles can be improved and carryover of reagents and the like can be prevented. Because the geometrical arrangement of the magnets 41 does not change during a series of processes in the determination process, mounting or demounting of the cuvette 31 does not affect magnetic fields applied to the other cuvettes 31 mounted on the reaction disk 11.

[Modification]

An automatic analyzer according to a modification of the present embodiment will be described. In an automatic analyzer according to the above embodiment, the magnetic flux density of a magnetic field in a test solution is made spatially substantially uniform by mounting the magnet 41 having the magnet front surface 41*f* larger than the test solution contact surface 31*c*. The automatic analyzer according to the modification is mounted with, in addition to magnets to generate a magnetic field in the test solution, ferromagnetic substances to enhance spatial uniformity of a magnetic field in the test solution. An automatic analyzer according to a modification of the modification will be described below. In the description that follows, the same reference signs are attached to elements having substantially the same function as those in the above embodiment and a duplicate description will be provided only when necessary.

FIG. 25A is a diagram schematically showing an arrangement example of a magnet 61 and a ferromagnetic substance 63 according to the modification and a diagram of the cuvette 31 viewed from the Y direction. FIG. 25B is a diagram of the cuvette 31 in FIG. 25A viewed from the X direction. In FIG. 25B, an illustration of lines of magnetic force is omitted for the sake of simplicity. As shown in FIGS. 25A and 25B, two magnets 61-1, 61-2 are arranged like sandwiching the cuvette 31 therebetween in the X direction. It is assumed that the magnet 61-1 is magnetized as an N pole and the magnet 61-2 is magnetized as an S pole. Lines of magnetic force from the magnet 61-1 to the magnet 61-2 are ideally straight lines along the X axis. Light from the light source 210 of the photometric mechanism 27 travels along the Y axis. Here, two faces perpendicular to the light path of four side faces of the cuvette 31 are called light path faces and two faces parallel to the light path are called non-light path faces. That is, the two magnets 61-1, 61-2 are provided on the non-light path face sides of the cuvette 31. Hereinafter, when the magnets 61-1, 61-2 are not distinguished, the magnets are simply written as the magnets 61.

Each of the magnets 61 has substantially the same size as that of a conventional magnet. That is, the size of the magnet front surface of the magnet 61 is not larger than the size of the test solution contact surface. Therefore, lines of magnetic force of a magnetic field generated by the magnet 61 is significantly distorted in the periphery of the cuvette 31. In other words, the magnetic field density of a magnetic field generated by the magnet 61 is extremely degraded in the periphery when compared with the center portion of the cuvette 31.

In the modification, the ferromagnetic substance 63 to enhance spatial uniformity of the magnetic flux density is arranged around the cuvette 31. The ferromagnetic substance 63 includes a substance that draws lines of magnetic force of a magnetic field generated from the magnet 61. Any substance whose magnetic susceptibility is relatively large is applicable as the ferromagnetic substance 63. For example, a lump of iron (hereinafter, called an iron piece) may be used as the ferromagnetic substance 63. The geometrical arrangement such as the installation location, size, shape, number and the like of the iron piece 63 is decided such that spatial uniformity of the magnetic flux density of a magnetic field generated by the magnet 61 is enhanced. The geometrical arrangement of the iron piece 63 may optimally be decided by a simulation or the like.

For example, the iron piece 63 in FIGS. 25A and 25B is provided on the bottom side of the cuvette 31. Accordingly, lines of magnetic force from the magnet 61-1 to the magnet 61-2 in the X-axis direction can be made a substantially straight line. The arrangement location of the iron piece 63 is not particularly limited and, in addition to the bottom side of the cuvette 31, the iron piece may be arranged on an optical path face side, a non-optical path face side, or an opening side. However, light from the light source 210 of the photometric mechanism 27 may be blocked. Therefore, when the iron piece 63 is arranged on the optical path face side, the geometrical arrangement such as the installation location, size, shape, number and the like of the iron piece 63 may be decided such that light from the light source 210 can reach the detector 220. For example, each of iron pieces 63-1, 63-2 may be arranged on the upper side and the lower side sandwiching the optical path therebetween on the optical path face side so as to avoid crossing the optical path of light or a through hole to allow light to pass through may be provided.

Next, another arrangement example of an iron piece 65 will be described with reference to FIGS. 26A and 26B. FIG. 26A is a diagram schematically showing an arrangement example of the magnet 61 and the iron piece 65 according to another arrangement example and a diagram of the cuvette 31 viewed from above. FIG. 26B is a diagram of the cuvette 31 in FIG. 26A viewed from the Y direction. As shown in FIGS. 26A and 26B, the iron piece 65 has a geometrical arrangement such that lines of magnetic force of a magnetic field generated by the magnet 61 form a closed circuit via the magnet 61 and the iron piece 65. To be concrete, the iron piece 65 is in contact with both of the magnets 61-1, 61-2 and is arranged like surrounding the magnet arrangement face and the bottom of the cuvette 31. When a closed circuit is formed, compared with non-closed circuits in FIGS. 25A and 25B, a leakage magnetic field to the outside of the magnet 61 can be reduced. Therefore, by forming a closed circuit using the iron piece 65, spatial uniformity of the magnetic flux density can further be enhanced.

In FIGS. 26A and 26B, the iron piece 65 is provided like surrounding the magnet arrangement face and the bottom of the cuvette 31. However, the present embodiment is not limited to such an example. For example, the iron piece 65 may be provided like surrounding four side faces (magnet arrangement faces and magnet non-arrangement faces) and the bottom of the cuvette 31. In this case, as described above, the geometrical arrangement of the iron piece may be decided such that light from the light source 210 of the photometric mechanism 27 is not blocked.

According to the modification, therefore, the magnetic flux density of a magnetic field from a magnet can be made spatially substantially uniform without increasing the size of the magnet. In the case of the modification, compared with a case of increasing the size of a magnet, the manufacturing cost and discarding cost of the magnet can be reduced.

Incidentally, the above geometrical arrangement of the iron piece is only by way of example. If spatial uniformity of the magnetic flux density of a magnetic field by the magnet 61 can be enhanced, the geometrical arrangement of an iron piece can arbitrarily be decided. For example, the iron piece may be provided above the cuvette 31 so as to block the opening of the cuvette 31. In this case, the iron piece may be withdrawn from above the cuvette 31 when a specimen is dispensed into the cuvette 31 or the cuvette 31 is cleaned.

To further enhance spatial uniformity of the magnetic flux density, the cuvette may be surrounded by the iron piece without providing a notch for the optical path. In this case, optical measurements of the test solution by the photometric mechanism 27 may be made in the transport mechanism 57, instead of the reaction disk 11. In this case, the transport mechanism 57 is provided with the photometric mechanism 27. Then, the cuvette 31 accommodating the test solution to be optically measured may be moved from the reaction disk 11 to the transport mechanism 57 to make optical measurements of the test solution by the photometric mechanism 27 in the transport mechanism 57. Accordingly, spatial uniformity of the magnetic flux density can further be enhanced.

[General Remarks]

An automatic analyzer according to the present embodiment includes the reaction disk 11, a magnetic field generator, and the photometric mechanism 27. The reaction disk 11 accommodates the cuvette 31 for the test solution containing a sample and magnetic particles. The magnetic field generator applies a magnetic field to the test solution in the cuvette 31. The photometric mechanism 27 includes the light source 210 and the detector 220. The light source 210 irradiates light toward the test solution in the cuvette 31. The detector 220 is provided in a position opposed to the light source 210 across the cuvette 31 to detect light from the test solution. The magnetic field generator has a geometrical arrangement such that the magnetic flux density of a magnetic field in the test solution inside the cuvette 31 is substantially uniform. To be concrete, the magnetic field generator is roughly divided into two types. The first type of the magnetic field generator has the magnet 41. The magnets 41 have a geometrical arrangement such that the magnetic flux density of the magnetic field in the test solution inside the cuvette 31 is substantially uniform. As the magnet 41, a magnet having the magnet front surface 41f larger than the test solution contact surface 31c of the cuvette 31 is used. In addition, the magnets 41 are arranged such that the difference h of height between the photometry position and the lower end of the magnet 41 becomes larger than the distance d between magnets. The second type of the magnetic field generator has the magnet 61 and the ferromagnetic substance 63 or the ferromagnetic substance 65. The magnet 61 generates a magnetic field applied to the test solution and the ferromagnetic substance 63 or the ferromagnetic substance 65 has a geometrical arrangement such that the magnetic flux density of the magnetic field in the test solution inside the cuvette 31 is substantially uniform.

If the above configuration is adopted, magnetic particles can be separated from the test solution by a magnetic force caused by the magnet 41 or the magnet 61 while the concentration distribution of magnetic particles in the test solution is maintained uniform. As a result, variations of measured values caused by changes of the liquid volume of the test solution or the photometry position can be reduced and the influence on measurement results can be inhibited. Therefore, the automatic analyzer 1 according to the present embodiment can obtain high-precision inspection results. In addition, the development cost of the automatic analyzer 1 can be reduced. Even if the relative physical relationship of the test solution and the magnet 41 or the magnet 61 varies among the different cuvettes 31 due to producing tolerances of the size of the cuvette 31 or the fixing position, variations of inspection results among the different cuvettes 31 can be reduced.

Therefore, according to the present embodiment, obtaining high-precision inspection results from an automatic analyzer that determines molecules to be detected by optically measuring turbidity or absorbance of a test solution derived directly from magnetic particles is realized.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An automatic analyzer comprising:
a disk configured to accommodate a plurality of cuvettes;
a magnetic field generator configured to generate a magnetic field applied to a test solution containing a sample and magnetic particles accommodated in each of the cuvettes; and
a photometric mechanism configured to include a light source that irradiates light toward the test solution and a detector provided in a position opposed to the light source across the cuvette to detect the light from the test solution, wherein
the magnetic field generator includes a first magnet and a second magnet arranged opposite to each other across each of the cuvettes in the disk such that they are substantially perpendicular to a direction of incident light from the light source wherein a magnetic flux density of the magnetic field generated between the first and second magnets in the test solution inside the cuvette becomes substantially uniform, and
the first magnet and second magnet are each formed of a permanent magnet plate and a soft magnetic plate formed from a soft magnetic material, wherein the soft magnetic plate is arranged between the side of the permanent magnet plate and the side of the cuvette.

2. The automatic analyzer according to claim 1, wherein the applying direction is a direction that crosses both of the incident direction and a major axis of the cuvette.

3. The automatic analyzer according to claim 1, wherein the magnetic flux density of the magnetic field on the axis in the test solution is 0.1 T or more.

4. The automatic analyzer according to claim 1, wherein fluctuations of the magnetic flux density of the magnetic field on the axis in the test solution is 0.04 T/mm or less.

5. The automatic analyzer according to claim 1, wherein a face opposed to the cuvette of each of the first magnet and the second magnet is larger than a contact portion with the test solution of an inner wall of the cuvette.

6. The automatic analyzer according to claim 5, wherein the contact portion is a portion with which the test solution having a maximum fluid volume set to the automatic analyzer is in contact in the inner wall of the cuvette.

7. The automatic analyzer according to claim 5, wherein a distance between the first magnet and the second magnet is equal to the distance between a photometry position on the cuvette and a lower end of the first magnet and the second magnet or less.

8. The automatic analyzer according to claim 1, wherein the cuvette contains no material having ferromagnetism.

9. The automatic analyzer according to claim 1, further comprising:
an attaching and detaching mechanism configured to detachably attach the cuvette to the disk.

10. The automatic analyzer according to claim 9, further comprising:
a stirring mechanism configured to stir the test solution in the cuvette using a stirrer;
a cleaning mechanism configured to clean the cuvette; and
a controller configured to control the photometric mechanism, the attaching and detaching mechanism, the stirring mechanism, and the cleaning mechanism, wherein
the controller
controls the stirring mechanism to stir the sample and the magnetic particles in the cuvette, controls the attaching and detaching mechanism to attach the stirred cuvette on the disk to apply the magnetic field,
controls the photometric mechanism to optically measure the test solution in the attached cuvette,
controls the attaching and detaching mechanism to detach the cuvette, in which the optical measurement with the photometric mechanism is ended, from the disk, and
controls the cleaning mechanism to clean the detached cuvette.

* * * * *